(12) United States Patent
Delmotte

(10) Patent No.: US 10,166,514 B2
(45) Date of Patent: Jan. 1, 2019

(54) DEVICE, SYSTEM AND METHOD FOR MIXING

(71) Applicants: BAXTER INTERNATIONAL INC., Deerfield, IL (US); BAXTER HEALTHCARE SA, Glattpark (opfikon) (CH)

(72) Inventor: Yves A. Delmotte, Neufmaison (BE)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 138 days.

(21) Appl. No.: 14/927,082

(22) Filed: Oct. 29, 2015

(65) Prior Publication Data
US 2016/0089642 A1 Mar. 31, 2016

Related U.S. Application Data

(63) Continuation of application No. 12/242,994, filed on Oct. 1, 2008, now abandoned, which is a
(Continued)

(51) Int. Cl.
B01F 5/06 (2006.01)
B01F 3/04 (2006.01)
(Continued)

(52) U.S. Cl.
CPC ............ B01F 3/04992 (2013.01); *A61K 9/12* (2013.01); *A61K 38/36* (2013.01); *B01F 5/0603* (2013.01);
(Continued)

(58) Field of Classification Search
CPC .............................. B01F 5/0691; B01F 5/0692
(Continued)

(56) References Cited

U.S. PATENT DOCUMENTS

| 49,345 A | 8/1865 | Hervey |
| 1,496,345 A | 6/1924 | Lichtenthaeler |

(Continued)

FOREIGN PATENT DOCUMENTS

| DE | 20307153 U1 | 9/2003 |
| EP | 0839498 A1 | 5/1998 |

(Continued)

OTHER PUBLICATIONS

Valblom, "Biofuels" (with Google machine translation) (Gembloux, Belgium). Downloaded from the Internet at <http://www.valbiom.be/index.php?url=fr/biocarburants/> (4 pp.) (applicant's internal files, known prior art).

(Continued)

*Primary Examiner* — David L Sorkin
(74) *Attorney, Agent, or Firm* — K&L Gates LLP

(57) ABSTRACT

A device or system includes a mixer comprising a three-dimensional lattice defining a plurality of tortuous, interconnecting passages therethrough. The mixer is in communication with sources or streams of at least two separate components which, when mixed, form a combined fluid stream. The sources or streams may be, at least initially, on opposite sides of the mixer, or the sources or streams may be on the upstream side of the mixer with an outlet disposed downstream of the mixer. A related method may include providing a mixer comprising a three-dimensional lattice defining a plurality of tortuous, interconnecting passages therethrough, and selecting a material for the mixer based on physical characteristics of said material, said characteristics including a selected one or more of mean flow pore size, thickness and porosity volume.

20 Claims, 24 Drawing Sheets

Related U.S. Application Data continuation-in-part of application No. 11/624,113, filed on Jan. 17, 2007, now abandoned.

(60) Provisional application No. 60/759,695, filed on Jan. 17, 2006.

(51) Int. Cl.
  *B01F 11/00* (2006.01)
  *B01F 13/00* (2006.01)
  *A61K 9/12* (2006.01)
  *A61K 38/36* (2006.01)
  *B01F 15/00* (2006.01)

(52) U.S. Cl.
  CPC .......... *B01F 5/0682* (2013.01); *B01F 5/0691* (2013.01); *B01F 11/0071* (2013.01); *B01F 13/002* (2013.01); *B01F 13/0023* (2013.01); *B01F 15/0087* (2013.01); *B01F 2215/0032* (2013.01); *B01F 2215/0034* (2013.01); *B01F 2215/0436* (2013.01); *Y10T 137/87652* (2015.04)

(58) Field of Classification Search
  USPC .......................... 366/176.3, 181.5, 336, 340
  See application file for complete search history.

(56) References Cited

U.S. PATENT DOCUMENTS

| | | | |
|---|---|---|---|
| 2,584,827 A | | 2/1952 | Bailey |
| 2,747,844 A | | 5/1956 | Slayter |
| 2,802,648 A | * | 8/1957 | Christensen .......... G05D 11/132 222/389 |
| 2,995,309 A | * | 8/1961 | Moen .................... B67D 1/1416 239/343 |
| 3,409,042 A | * | 11/1968 | Anthony ................. F16K 19/00 137/603 |
| 3,861,652 A | | 1/1975 | Clark et al. |
| 3,884,388 A | * | 5/1975 | Holcomb .............. B01F 5/0256 222/132 |
| 4,068,830 A | | 1/1978 | Gray |
| 4,316,673 A | | 2/1982 | Speer |
| 4,329,067 A | | 5/1982 | Goudy, Jr. |
| 4,475,821 A | * | 10/1984 | Koch .................... B01D 15/166 138/38 |
| 4,538,920 A | | 9/1985 | Drake |
| 4,568,725 A | | 2/1986 | Boisson et al. |
| 4,631,055 A | | 12/1986 | Redl et al. |
| 4,846,405 A | | 7/1989 | Zimmermann |
| 4,978,336 A | | 12/1990 | Capozzi et al. |
| 5,116,315 A | | 5/1992 | Capozzi et al. |
| 5,364,595 A | | 11/1994 | Smith |
| 5,368,563 A | | 11/1994 | Lonneman et al. |
| 5,393,502 A | | 2/1995 | Miller et al. |
| 5,443,183 A | | 8/1995 | Jacobsen et al. |
| 5,474,540 A | | 12/1995 | Miller et al. |
| 5,531,683 A | | 7/1996 | Kriesel et al. |
| 5,556,580 A | | 9/1996 | Suddith |
| 5,582,596 A | | 12/1996 | Fukunaga et al. |
| 5,605,255 A | | 2/1997 | Reidel et al. |
| 5,614,153 A | | 3/1997 | Homberg |
| 5,665,067 A | | 9/1997 | Linder et al. |
| 5,788,670 A | | 8/1998 | Reinhard et al. |
| 5,814,022 A | | 9/1998 | Antanavich et al. |
| 5,989,215 A | | 11/1999 | Delmotte et al. |
| 6,045,757 A | | 4/2000 | Moriarty et al. |
| 6,054,122 A | | 4/2000 | MacPhee et al. |
| 6,062,722 A | | 5/2000 | Lake |
| 6,074,663 A | | 6/2000 | Delmotte et al. |
| 6,132,396 A | | 10/2000 | Antanavich et al. |
| 6,186,982 B1 | | 2/2001 | Gross et al. |
| 6,221,405 B1 | | 4/2001 | Sheehy et al. |
| 6,328,229 B1 | | 12/2001 | Duronio et al. |
| 6,383,422 B1 | | 5/2002 | Hoffschmidt |
| 6,454,739 B1 | | 9/2002 | Chang |
| 6,461,325 B1 | | 10/2002 | Delmotte et al. |
| 6,461,361 B1 | | 10/2002 | Epstein |
| 6,548,729 B1 | | 4/2003 | Seelich et al. |
| 6,561,200 B1 | | 5/2003 | Fournel et al. |
| 6,562,002 B1 | | 5/2003 | Taylor |
| 6,566,145 B2 | | 5/2003 | Brewer |
| 6,585,696 B2 | | 7/2003 | Petersen et al. |
| 6,599,515 B1 | | 7/2003 | Delmotte |
| 6,620,125 B1 | | 9/2003 | Redl |
| 6,802,822 B1 | | 10/2004 | Dodge |
| 6,835,186 B1 | | 12/2004 | Pennington et al. |
| 6,883,958 B2 | | 4/2005 | Mayer |
| 6,884,232 B1 | | 4/2005 | Hagmann et al. |
| 6,887,974 B2 | | 5/2005 | Pathak |
| 6,921,381 B2 | | 7/2005 | Spero et al. |
| 6,965,014 B1 | | 11/2005 | Delmotte et al. |
| 6,979,426 B2 | | 12/2005 | Teall et al. |
| 6,982,100 B2 | | 1/2006 | Swearingen et al. |
| 7,007,636 B2 | | 3/2006 | Schlesser et al. |
| 7,018,970 B2 | | 3/2006 | Hsu et al. |
| 7,033,634 B2 | | 4/2006 | Engesser et al. |
| 7,037,538 B2 | | 5/2006 | O'Sullivan et al. |
| 7,045,060 B1 | | 5/2006 | Liles et al. |
| 7,064,156 B2 | | 6/2006 | Rink et al. |
| 7,074,977 B2 | | 7/2006 | Rapier et al. |
| 7,077,835 B2 | | 7/2006 | Robinson et al. |
| 7,105,151 B2 | | 9/2006 | Unger et al. |
| 7,115,192 B1 | | 10/2006 | Vanden Bussche et al. |
| 7,118,721 B2 | | 10/2006 | Rini et al. |
| 7,125,909 B2 | | 10/2006 | Jones et al. |
| 7,128,276 B2 | | 10/2006 | Nilsen et al. |
| 7,128,885 B2 | | 10/2006 | Satchel, Jr. |
| 7,135,027 B2 | | 11/2006 | Delmotte |
| 7,135,108 B1 | | 11/2006 | Barnes |
| 7,135,554 B1 | | 11/2006 | Page et al. |
| 7,140,292 B2 | | 11/2006 | Parsons et al. |
| 7,141,613 B2 | | 11/2006 | Albach et al. |
| 7,144,148 B2 | | 12/2006 | Reed et al. |
| 7,144,170 B2 | | 12/2006 | Parks et al. |
| 7,144,552 B1 | | 12/2006 | Fukuizumi et al. |
| 7,144,568 B2 | | 12/2006 | Ricard et al. |
| 7,144,663 B2 | | 12/2006 | Sano et al. |
| 7,166,651 B2 | | 1/2007 | Qian |
| 7,166,670 B2 | | 1/2007 | Udding et al. |
| 7,175,337 B2 | | 2/2007 | Bergman |
| 7,175,874 B1 | | 2/2007 | Pacetti |
| 7,179,413 B1 | | 2/2007 | Shin et al. |
| 7,179,882 B2 | | 2/2007 | Adkins et al. |
| 7,186,419 B2 | | 3/2007 | Petersen |
| 7,186,435 B2 | | 3/2007 | Beckett et al. |
| 7,189,385 B2 | | 3/2007 | Montgomery |
| 7,192,599 B2 | | 3/2007 | Mercier et al. |
| 7,198,769 B2 | | 4/2007 | Cichanowicz |
| 7,201,934 B2 | | 4/2007 | Nijhuis et al. |
| 7,202,301 B2 | | 4/2007 | Ando et al. |
| 7,211,651 B2 | | 5/2007 | Pathak |
| 7,214,726 B2 | | 5/2007 | Qian |
| 7,217,442 B2 | | 5/2007 | Wilt et al. |
| 7,220,048 B2 | | 5/2007 | Kohlgruber et al. |
| 7,223,307 B2 | | 5/2007 | Lenius |
| 7,229,663 B2 | | 6/2007 | Stephenson et al. |
| 7,235,217 B2 | | 6/2007 | Nguyen |
| 7,237,693 B2 | | 7/2007 | Brennan et al. |
| 7,237,767 B2 | | 7/2007 | Sakakibara et al. |
| 7,238,467 B2 | | 7/2007 | Ikeda et al. |
| 7,238,749 B2 | | 7/2007 | Buergel et al. |
| 7,240,483 B2 | | 7/2007 | Cizeron et al. |
| 7,246,631 B2 | | 7/2007 | Georgeson et al. |
| 7,247,609 B2 | | 7/2007 | Lutolf et al. |
| 7,249,574 B2 | | 7/2007 | Verstallen |
| 7,252,847 B2 | | 8/2007 | Keller et al. |
| 7,257,985 B2 | | 8/2007 | Franda et al. |
| 7,258,144 B2 | | 8/2007 | Barthod et al. |
| 7,264,231 B2 | | 9/2007 | Kojima |
| 7,264,394 B1 | | 9/2007 | Liles |
| 7,264,732 B2 | | 9/2007 | Bradley |
| 7,265,190 B2 | | 9/2007 | Dairoku et al. |

(56) References Cited

U.S. PATENT DOCUMENTS

| | | | |
|---|---|---|---|
| 7,265,895 | B2 | 9/2007 | Miyazaki et al. |
| 7,267,232 | B2 | 9/2007 | Khan et al. |
| 7,268,206 | B2 | 9/2007 | Galewski et al. |
| 7,281,844 | B2 | 10/2007 | Glanville |
| 7,284,902 | B2 | 10/2007 | Hosozawa |
| 7,285,402 | B2 | 10/2007 | Gaddy et al. |
| 7,285,698 | B2 | 10/2007 | Liu et al. |
| 7,288,322 | B2 | 10/2007 | Bosshammer |
| 7,288,620 | B2 | 10/2007 | Galewski |
| 7,290,960 | B2 | 11/2007 | Sengupta et al. |
| 7,291,673 | B2 | 11/2007 | Hubbell et al. |
| 7,294,681 | B2 | 11/2007 | Jiang et al. |
| 7,306,130 | B2 | 12/2007 | Brugner |
| 7,311,265 | B2 | 12/2007 | Bhatia |
| 7,314,957 | B2 | 1/2008 | Codignola |
| 7,318,324 | B2 | 1/2008 | Ulrich et al. |
| 7,323,437 | B2 | 1/2008 | Fujinami et al. |
| 7,323,505 | B2 | 1/2008 | Thibaut |
| 7,323,597 | B2 | 1/2008 | Hugo et al. |
| 7,324,746 | B2 | 1/2008 | Tanaka et al. |
| 7,325,967 | B2 | 2/2008 | Hoff et al. |
| 7,325,970 | B2 | 2/2008 | Keller |
| 7,326,379 | B2 | 2/2008 | Hasegawa et al. |
| 7,326,816 | B2 | 2/2008 | Knauf et al. |
| 7,328,549 | B2 | 2/2008 | Kinney et al. |
| 7,331,483 | B2 | 2/2008 | Bhimani et al. |
| 7,334,415 | B2 | 2/2008 | Krabbendam et al. |
| 7,335,805 | B2 | 2/2008 | Iikubo et al. |
| 7,338,543 | B2 | 3/2008 | Kikawa |
| 7,338,682 | B2 | 3/2008 | Marumo et al. |
| 7,338,924 | B2 | 3/2008 | Varadaraj |
| 7,339,080 | B2 | 3/2008 | Hugo et al. |
| 7,339,674 | B2 | 3/2008 | Wierzbicki et al. |
| 7,345,193 | B2 | 3/2008 | Makino et al. |
| 7,347,886 | B2 | 3/2008 | Ickinger |
| 7,351,753 | B2 | 4/2008 | Qian |
| 7,370,777 | B2 | 5/2008 | Hefele et al. |
| 7,371,300 | B2 | 5/2008 | Bain et al. |
| 7,371,395 | B2 | 5/2008 | Parisot et al. |
| 7,371,406 | B2 | 5/2008 | Ramstack et al. |
| 7,371,464 | B2 | 5/2008 | Sherman et al. |
| 7,374,156 | B2 | 5/2008 | Ooyachi et al. |
| 7,374,606 | B2 | 5/2008 | Sato et al. |
| 7,374,694 | B2 | 5/2008 | Gaudinot et al. |
| 7,375,191 | B2 | 5/2008 | Bellotti et al. |
| 7,381,259 | B2 | 6/2008 | Hanneman, Jr. et al. |
| 7,560,100 | B2 | 7/2009 | Pinchasi et al. |
| 7,906,118 | B2 | 3/2011 | Chang et al. |
| 2005/0142162 | A1 | 6/2005 | Hunter et al. |
| 2006/0009801 | A1 | 1/2006 | McGurk et al. |
| 2006/0191962 | A1 | 8/2006 | Redl et al. |
| 2008/0281271 | A1 | 11/2008 | Griffiths et al. |
| 2009/0038701 | A1 | 2/2009 | Delmotte |

FOREIGN PATENT DOCUMENTS

| | | | |
|---|---|---|---|
| EP | 2002882 | A1 | 12/2008 |
| GB | 2060420 | A | 5/1981 |
| JP | 4100528 | | 4/1992 |
| JP | 2000505670 | A | 5/2000 |
| JP | 2005246334 | A | 9/2005 |
| RU | 2191623 | C2 | 10/2002 |
| WO | WO-96/39212 | | 12/1996 |
| WO | WO-97/28834 | A1 | 8/1997 |
| WO | WO-97/39950 | | 10/1997 |
| WO | WO-00/51704 | A1 | 9/2000 |
| WO | WO-02/19843 | | 3/2002 |
| WO | WO-2004/024306 | | 3/2004 |
| WO | WO-2005/048977 | | 6/2005 |
| WO | WO-2005/048983 | A1 | 6/2005 |
| WO | WO-2007/084919 | A1 | 7/2007 |
| WO | WO-2007/130703 | | 11/2007 |
| WO | WO-2008/027821 | | 3/2008 |

OTHER PUBLICATIONS

The Associated Press, "Brazil Buys Into Flex-Fuel Cars; They Run on Gas, Ethanol or Any Combination", (Aug. 30, 2004) (2 pp.).
Cle de Determination: HVP as Engines (Updated Feb. 6, 2017) (with Google machine translation). Downloaded from the Internet at: http://www.oliomobile.org/forum/viewtopic.php?t+365 (10 pp.) (applicant's internal files, known prior art).
FX Technology and Products, "Fibrimex Product Concepts" (2004). Downloaded from the Internet at <http://www.fibrimex.com/product_concept.asp> (1 page).
3M ESPE,"Position™ Penta™ Quick VPS Alginate Replacement", (St. Paul, Minnesota). Downloaded from the Internet at <http://solutions.3m.com/wps/portal/3M/en_US/3M-ESPE/dental-professionals/products/category/impression/position-penta-quick/> (4 pp.) (applicant's internal files; known prior art).
Ford Motor Company, "Soy-Based Foam" (Dearborn, Michigan). Downloaded from the Internet at: <http://www.ford.com/innovation/automotive-technology/developing-better-ideas/soy-based-foam/soy-foam-623p> (1 page) (applicant's internal files; known prior art).
English translation of Official Action from corresponding Russian patent application No. 2008133574, dated Dec. 6, 2010.
European Search Report, European Patent Application No. 10075208.8, dated Jul. 2, 2010.
Examination Report, Australian Patent Application No. 2013213741, dated Aug. 25, 2015.
Examiner's report, Australian Patent Application No. 2007205932, dated Nov. 11, 2011.
First Office Action, Chinese Patent Application No. 201210091213.0, dated Dec. 10, 2013.
Gruber et al., "Alteration of fibrin network by activated protein C", *Blood*, 83:2541-8 (1994).
International Search Report for corresponding International Application No. PCT/US2007/060639, dated Jun. 1, 2007.
Notice of Preliminary Rejection, Korean Patent Application No. 10-2008-7017316, dated Apr. 17, 2013.
Notice of Reasons for Rejection, Japanese Patent Application No. 2008-551514, dated Mar. 19, 2013.
Notice of Reasons for Rejection, Japanese Patent Application No. 2008-551514, dated Mar. 2, 2012.
Office Action, Canadian Patent Application No. 2,632,608, dated Mar. 13, 2012.
Porex Porous Products Group, Interact w/Innovation . . . Discover the Advantages of Porex Catalog (Fairburn, GA) (circa 2005, 9 pp.).
Porex Porous Products Group, Mupor™ Membrane Applications Brief Catalog (Fairburn, Ga) (circa 2000, 7 pp.).
Porex Porous Products Group, Products & Services Catalog (Fairburn, GA) (circa 2002, 24 pp.).
Porvair Filtration Group Ltd., "Developments in porous polymeric materials", (Fareham, Hampshire UK) (Sep. 2005, 1 page).
Porvair Filtration Group, Sintered Porous Materials Catalog (Fareham, Hampshire, UK) (circa 2005, 7 pp.).
Porex Technologies, Healthcare Applications: Pipette (Fairburn, GA) (2006, 1 page).
Prateepchaikul et al., "Palm Oil as a Fuel for Agricultural Diesel Engines: Comparative Testing Against Diesel Oil", Songklanakarin Journal of Science and Technology, 25(3): 15 pp. (May-Jun. 2003).
Ronghou et al., "Alcohol and Cotton Oil as Alternative Fuels for Internal Combustion Engines", chapter 5 IN: NAN et al. (eds.), *Integrated Energy Systems in China: The Cold Northeastern Region Experience*, (1994, 44 pp.).
Second Office Action, Chinese Patent Application No. 200780002525.7, dated Jan. 26, 2011.
Sheehan et al., "A Look Back at the U.S. Department of Energy's Aquatic Species Program: Biodiesel from Algae", Golden, CO: National Renewable Energy Laboratory, 329 pp. (Jul. 1998).
Third Office Action, Chinese Patent Application No. 200780002525.7, dated Dec. 7, 2011.
Brazilian Office Action for related Brazilian Application No. PI0706629-5; action dated Feb. 5, 2018; (3 pages).

\* cited by examiner

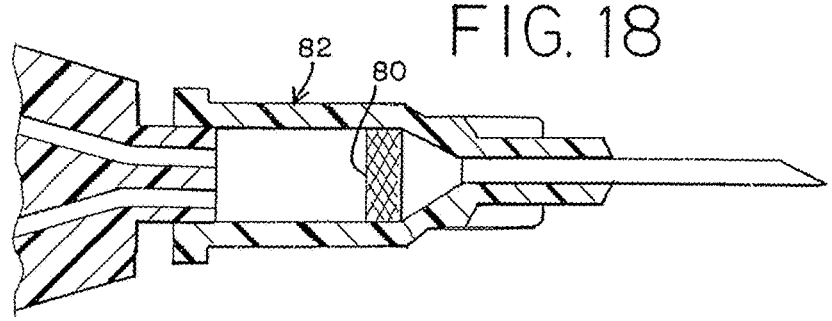
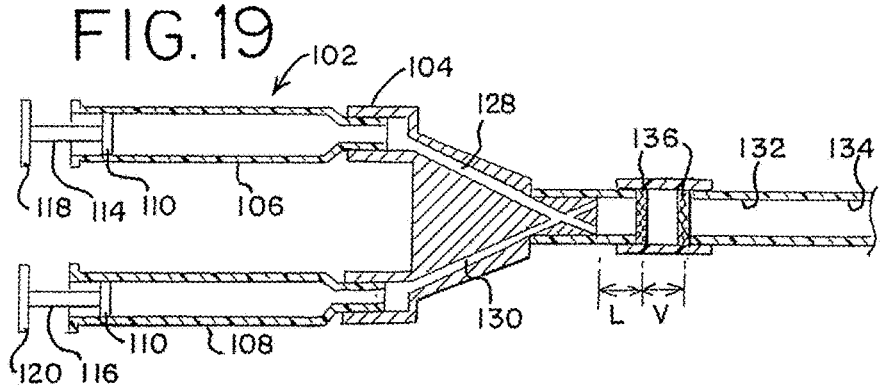
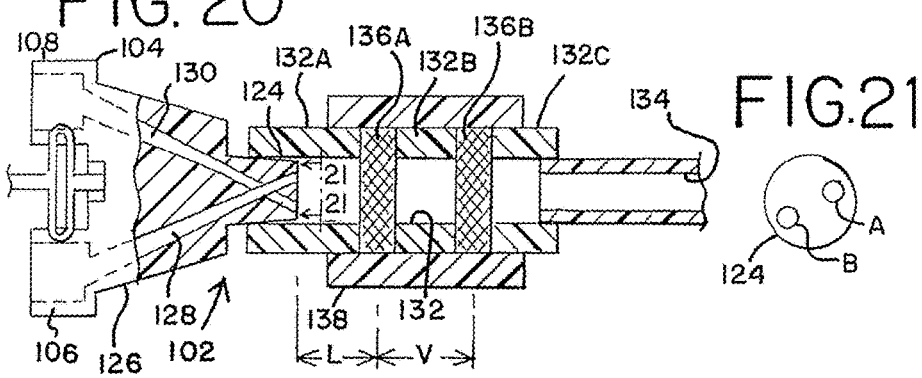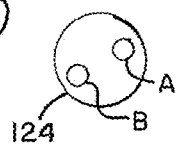

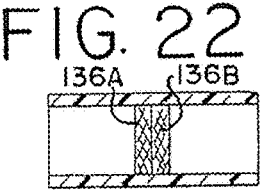
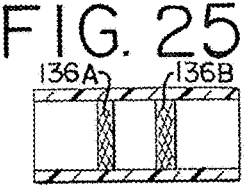
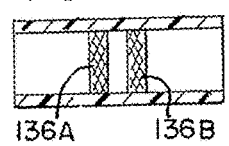
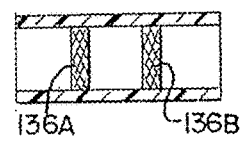
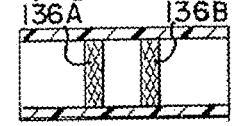
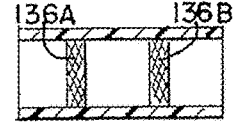
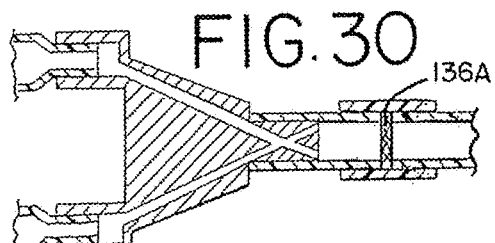
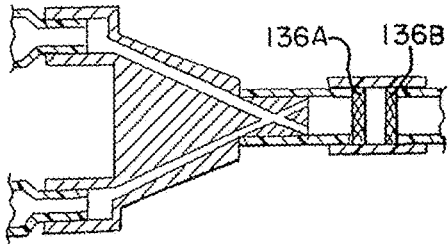
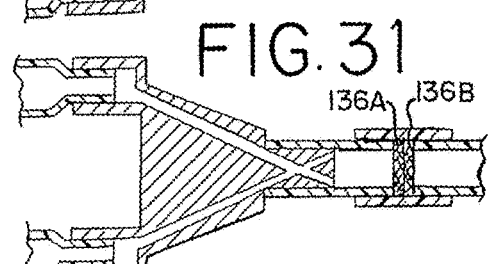
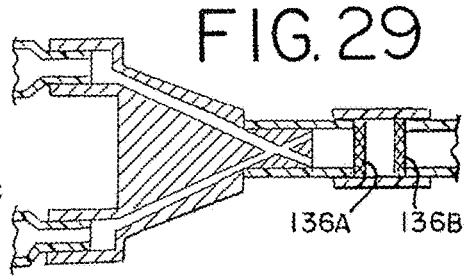
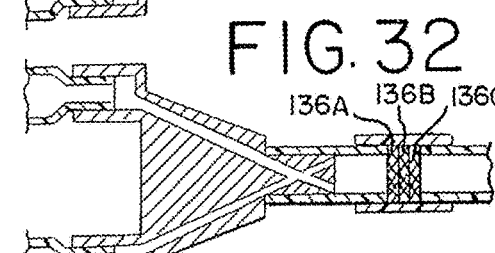

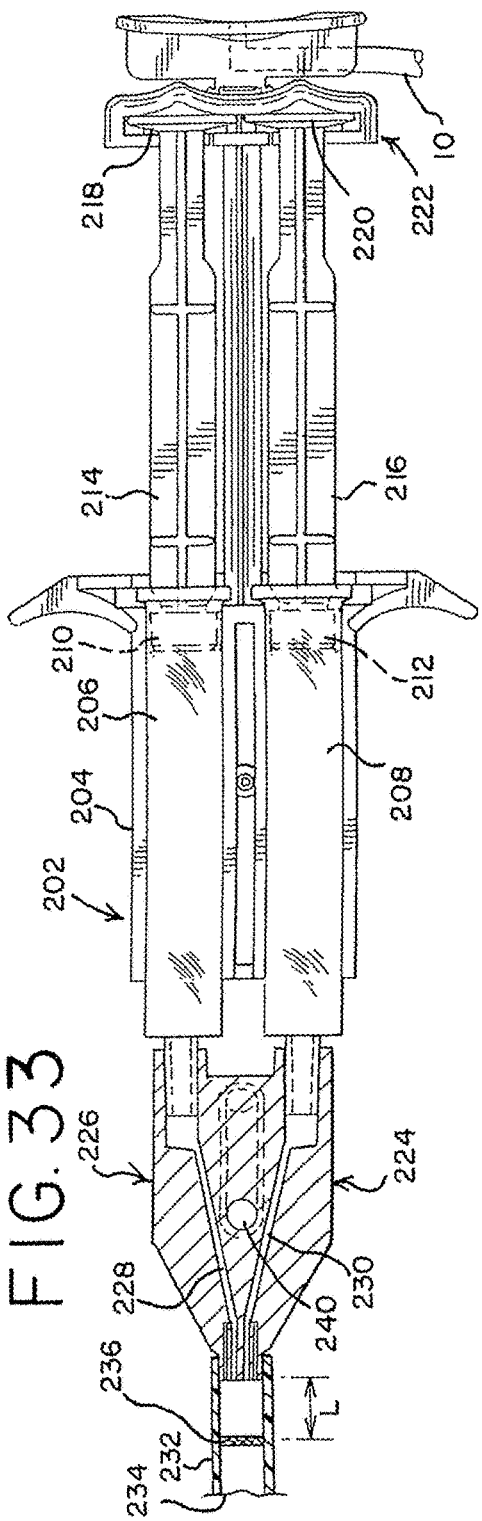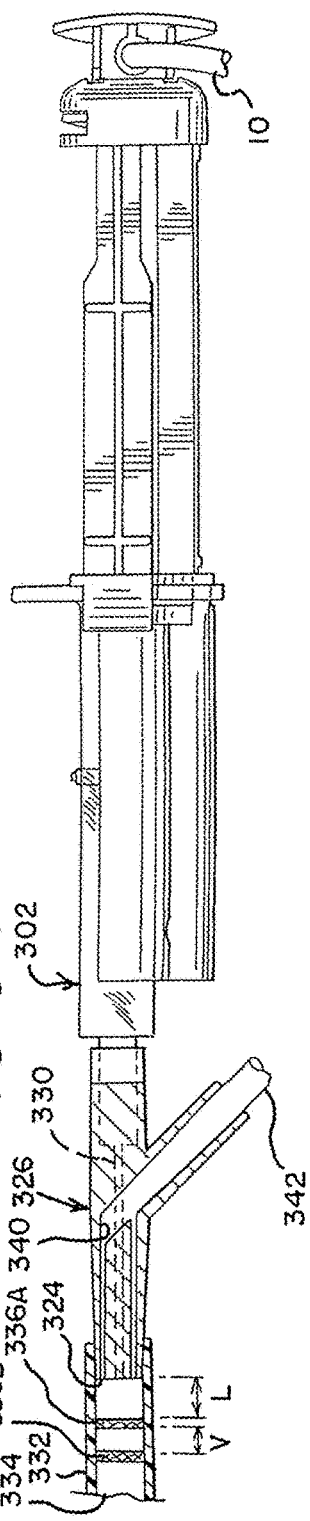

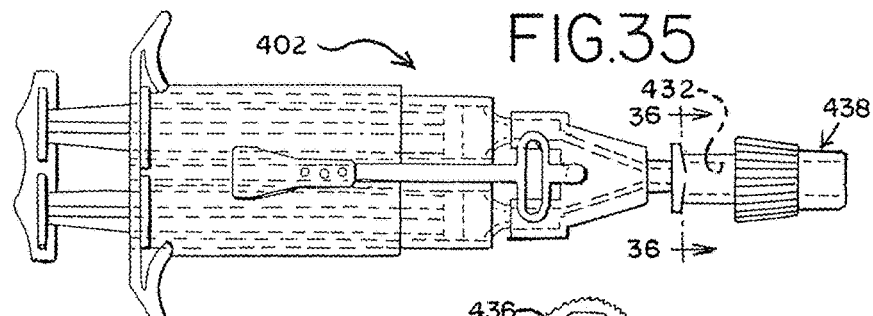
FIG.35
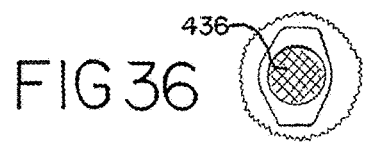
FIG.36
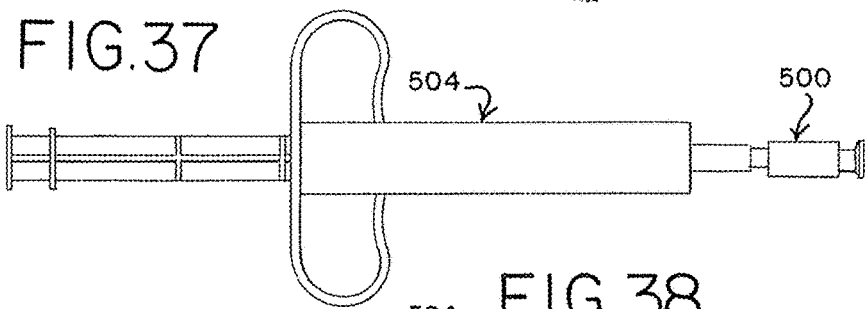
FIG.37
FIG.38
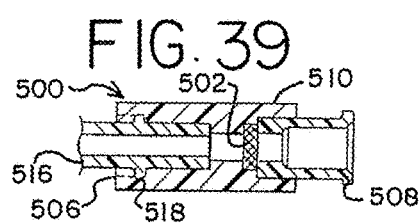
FIG.39
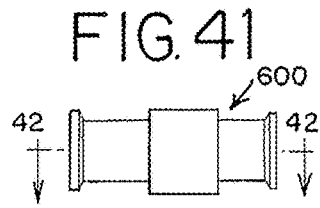
FIG.41
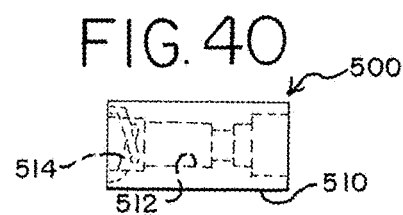
FIG.40
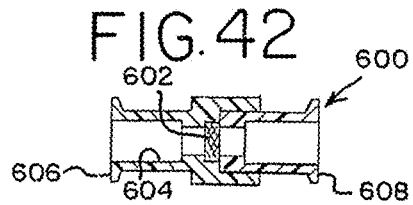
FIG.42

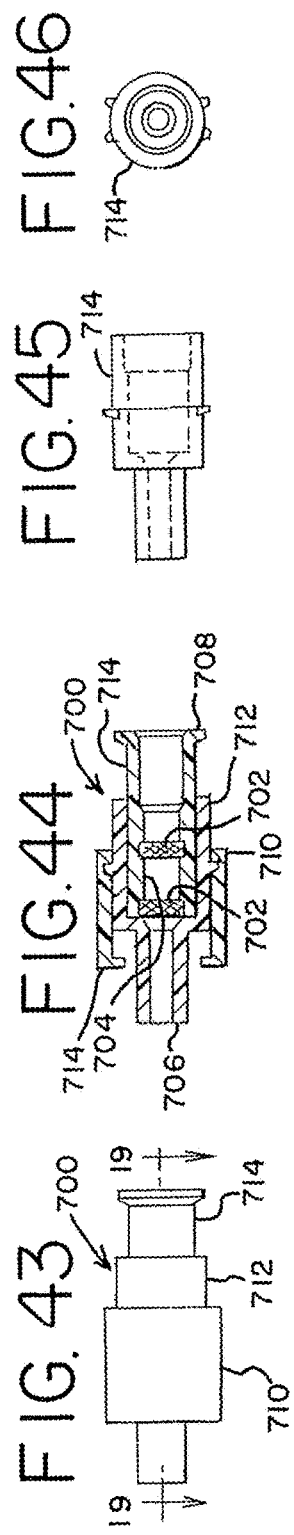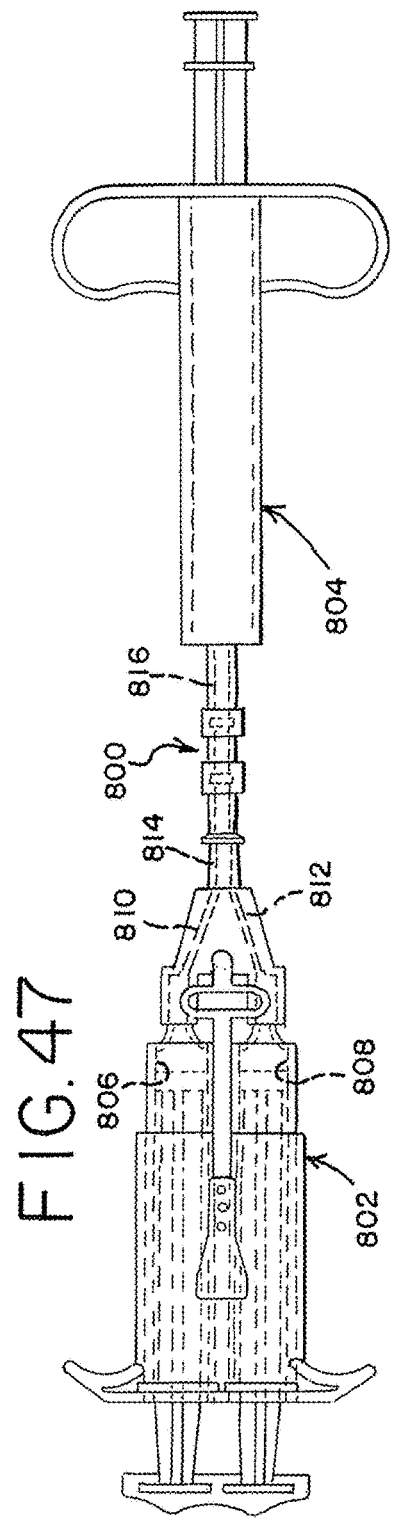

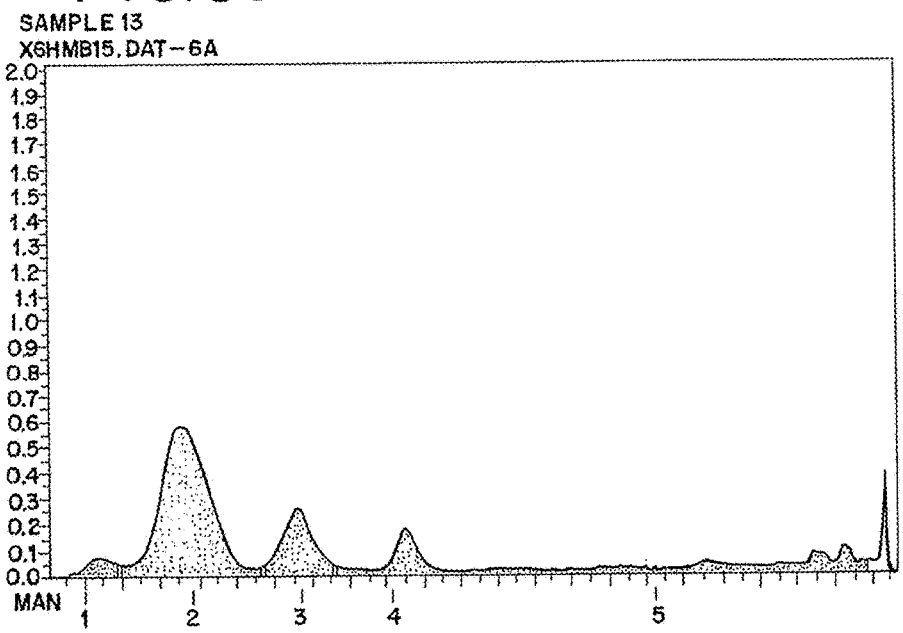
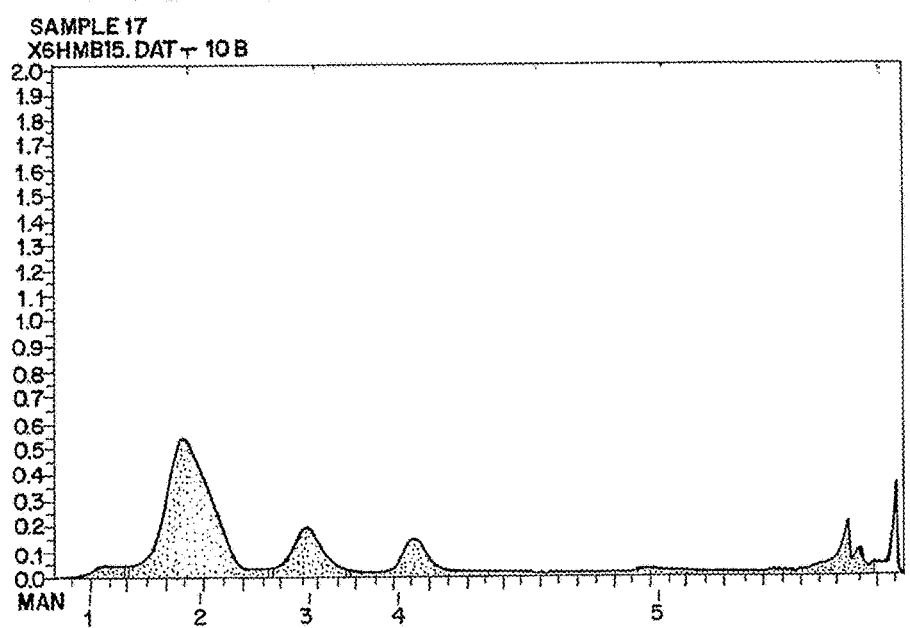

DEVICE, SYSTEM AND METHOD FOR MIXING

CROSS-REFERENCE TO RELATED APPLICATION

This application claims the benefit of and priority to U.S. patent application Ser. No. 12/242,994, filed Oct. 1, 2008, which is a continuation-in-part of U.S. patent application Ser. No. 11/624,113, filed Jan. 17, 2007, which claims priority to U.S. Provisional Patent Application No. 60/759,695, filed Jan. 17, 2006, each of which is hereby incorporated by reference herein, in its entirety and for all purposes.

BACKGROUND

This disclosure generally relates to an inline mixer for mixing multiple components of a combined fluid stream. In fact, this disclosure relates to such inline mixers, systems utilizing such inline mixers and methods of inline mixing in a variety of fields, including medicine, energy, manufacturing, etc.

Inline mixing of combined fluid streams, including fluid streams of different viscosities, may be useful in a wide variety of settings including the medical field, the food industry, electronics, automotive, energy, petroleum, pharmaceutical, chemical industries, manufacturing and others. In one example of an application in the medical field, inline mixing of two or more combined fluid streams is employed to form a sealant, such as a tissue sealant, that is applied to human and animal tissue. Such sealant may be employed to seal or repair tissue at a surgical or wound site, to stop bleeding, seal wounds, treat burns or skin grafts and a variety of other purposes. In the food industry, inline mixing of two or more components are useful for blending of food and beverage compositions. In the electronics and/or manufacturing industries, the combination of two or more components may be employed to create coatings or sealants as desired for particular applications. This may include coating or sealants that are optically clear, electrically conductive or insulative, thermally conductive or high temperature resistant or useful in very low temperature or cryogenic applications. In the ophthalmologic field, inline mixing of two or more components may be desirable to provide relatively small quantities or low flow rates of a treating agent for treatment of the eye. In the fuel or energy industries, inline mixing of air, water or other components with fuel may be helpful to create environmentally safer or cleaner fuels. Inline mixing may also be helpful in the manufacture of nano- or micro-sized particles and particle suspensions for use in the medical (such as drug delivery) field.

In the medical field, and more particularly in the field of tissue sealants used to seal or repair biological tissue, such sealant is typically formed from two or more components that, when mixed, form a sealant having sufficient adhesion for a desired application, such as to seal or repair skin or other tissue. Such sealant components are preferably biocompatible, and can be absorbed by the body, or are otherwise harmless to the body, so that they do not require later removal. For example, fibrin is a well known tissue sealant that is made from a combination of at least two primary components—fibrinogen and thrombin, which have, depending on the temperature, different viscosities of about 300 cps and 15 cps, respectively. Upon coming into contact with each other, the fibrinogen and thrombin components interact to form a tissue sealant, fibrin, which is extremely viscous.

Sealant components may be kept in separate containers and are combined prior to application. However, because sealant components such as fibrinogen and thrombin have different viscosities, complete and thorough mixing is often difficult to achieve. If the components are inadequately mixed, then the efficacy of the sealant to seal or bind tissue at the working surface is compromised.

Inadequate mixing of the type described above is also a problem present in other medical and/or non-medical fields, where two or more components having relatively different viscosities are required to be mixed together. Such components may tend to separate from each other prior to use or be dispensed in a less than thoroughly mixed stream, due at least in part to their different viscosities, flow rates and depending on the temperature and amount of time such mixture may be stored prior to use.

To overcome the difficulties of the formation of the highly viscous fibrin in the medical field, in providing tissue sealant, it has become common to provide in-line mixing of two or more components—in lieu of batch or tank mixing of the components—to form a tissue sealant, just prior to its application on a work surface. Some sealant products that may provide suitable mixtures include FLOSEAL, COSEAL, TISSEEL and ARTISS sealants from Baxter Healthcare Corporation, OMINEX sealants from Johnson & Johnson and BIOGLUE sealants from Cryolife, Inc. Such sealant may be applied by a dispenser that ejects sealant directly onto the tissue or other substrate or working surface. Examples of tissue sealant dispensers are shown in U.S. Pat. Nos. 4,631,055, 4,846,405, 5,116,315, 5,582,596, 5,665,067, 5,989,215, 6,461,361 and 6,585,696, 6,620,125 and 6,802,822 and PCT Publication No. WO 96/39212, all of which are incorporated herein by reference. Further examples of such dispensers also are sold under the Tissomat® and Duploject® trademarks, which are marketed by Baxter AG. Typically, in these prior art devices, two individual streams of the components fibrinogen and thrombin are combined and the combined stream is dispensed to the work surface. Combining the streams of fibrinogen and thrombin initiates the reaction that results in the formation of the fibrin sealant. While thorough mixing is important to fibrin formation, fouling or clogging of the dispenser tip can interfere with proper dispensing of fibrin. Such clogging or fouling may result from contact or mixing of the sealant components in a dispenser for an extended period of time prior to ejection of the sealant components from the dispensing tip.

In current mixing systems, the quality of mixing of two or more components having different viscosities may vary depending on the flow rate. For example, under certain flow conditions, the components may be dispensed as a less than thoroughly mixed stream. Accordingly, there is a desire to provide a mixing system which is not dependent on the flow rate to achieve sufficient mixing.

Although prior devices have functioned to various degrees in forming and dispensing mixtures, there is a continuing need to provide a mixer and dispensing system that provides reliable and thorough mixing of at least two components (such as, for example, for a tissue sealant) for application to a desired work surface or other use applications in other fields. Such a mixing system could be provided to dispense the mixture just prior to or at least in close proximity to its intended use or application. Preferably, such a mixer and dispensing system would also avoid undue fouling or clogging of the dispenser.

SUMMARY

In one aspect, the present disclosure is directed to a device for mixing at least two separate streams of components which, when mixed, form a combined fluid stream. The device includes a first passageway adapted to communicate with one of the at least two separate streams, and a second passageway adapted to communicate with another of the at least two separate streams. The device also includes a mixer communicating with each of the first and second passageways comprising a three-dimensional lattice defining a plurality of tortuous, interconnecting passages therethrough. The mixer has physical characteristics to sufficiently mix the component streams of the combined fluid stream, which characteristics include a selected one or more of mean flow pore size, thickness and porosity.

In another aspect, the present disclosure is directed to a system for combining at least two separate streams of components which, when mixed, form a combined fluid stream. The system includes a first passageway in fluid communication with one of the at least two separate streams, a second passageway in fluid communication with another of the at least two separate streams, and a third passageway in fluid communication with and downstream of the first and second passageways for joining the at least two separate streams at a selected location. The system also includes at least one mixer downstream of and in the vicinity of the selected location, the mixer comprising a three-dimensional lattice defining a plurality of tortuous, interconnecting passages therethrough. Additionally, the system includes an outlet downstream of the mixer to allow flow of the combined fluid stream.

In a further aspect, the present disclosure is directed to a system for mixing at least two separate components which, when mixed, form a combined fluid stream. The system includes at least one mixer having first and second sides and comprising a three-dimensional lattice defining a plurality of tortuous, interconnecting passages therethrough, a first port in fluid communication with the first side of the mixer and adapted to communicate with a source of a first component, and a second port in fluid communication with the second side of the mixer and adapted to communicate with a source of a second component. Each port is in fluid communication with the other port through the mixer to allow one of the first and second components to flow from selected one of the first and second sides of the mixer to the other side and to allow return flow of both the first and second components from the other side through the mixer.

In a still further aspect, the present disclosure is directed to a method for combining at least two separate components. The method includes providing a mixer comprising a three-dimensional lattice defining a plurality of tortuous, interconnecting passages therethrough, and selecting a material for the mixer based on physical characteristics of said material, said characteristics including a selected one or more of mean flow pore size, thickness and porosity volume.

A more detailed description of these and other aspects of the devices, systems, methods and compositions of the present disclosure is set forth below.

Although described later in terms of certain structures, it should be understood that the device, system and method of the present invention are not limited to the identical structures shown, and that the scope of the present invention is defined by the claims as now or hereafter filed.

BRIEF DESCRIPTION OF THE DRAWINGS

FIG. 18 is a partial cross-section view of a tissue sealant dispenser employing a modified distal end portion.

FIG. 19 is a partial cross-sectional view of another embodiment of a tissue sealant dispenser set forth in the present disclosure.

FIG. 20 is an enlarged cross-sectional view of the distal portion of the dispenser shown in FIG. 19.

FIG. 21 is a cross section taken along line 21-21 of FIG. 20 with a mixing portion removed.

FIG. 22 is an enlarged side view, similar to FIG. 2, but two mixers with no spacing between the mixers.

FIGS. 23-27 are enlarged side views, similar to FIG. 2, except showing a different mixer arrangement having two mixers with different relative spacing between the mixers.

FIGS. 28-29 are side views, similar to FIG. 20, except showing several different dispenser tips with two-mixer arrangements having different relative spacing between the mixers.

FIGS. 30-32 are side views, similar to FIG. 20, except showing several different dispenser tips with mixer arrangements having one, two or three mixers with no spacing between the mixers.

FIG. 33 is a partial cross-sectional view of another embodiment of a dispenser set forth in the present disclosure.

FIG. 34 is a partial cross-sectional view of a further embodiment of a tissue sealant dispenser set forth in the present disclosure.

FIG. 35 is a top view of a yet further embodiment of a tissue sealant dispenser set forth in the present disclosure.

FIG. 36 is a cross section taken along line 36-36 of FIG. 35.

FIG. 37 is a top view of a modified embodiment of a tissue sealant dispenser having a single mixing device connected to a dispensing device with a single container set forth in the disclosure.

FIG. 38 is a cross section of the tissue sealant dispenser of FIG. 37.

FIG. 39 is an enlarged cross section of a portion of the dispenser in FIG. 37, showing other portions removed.

FIG. 40 is a side view of a portion of the dispenser in FIG. 39 showing additional portions removed.

FIG. 41 is an side view of a modified mixing device shown disconnected from a dispensing apparatus.

FIG. 42 is a cross section taken along 42-42 of FIG. 41.

FIG. 43 is a side view of another mixing device shown disconnected from a dispensing apparatus.

FIG. 44 is a cross section taken along 44-44 of FIG. 43.

FIG. 45 is a side view of a portion of the dispenser in FIG. 44 showing additional portions removed.

FIG. 46 is a right end view of FIG. 45.

FIG. 47 is a top view of an arrangement that includes two dispensing devices connected by one of the mixing devices shown in FIGS. 39-46.

FIG. 57-60 are graphs showing the amount of constituent components present in respective samples of fibrinogen and three different fibrin mixtures each employing a different dispensing apparatus.

DETAILED DESCRIPTION

Figure 1:
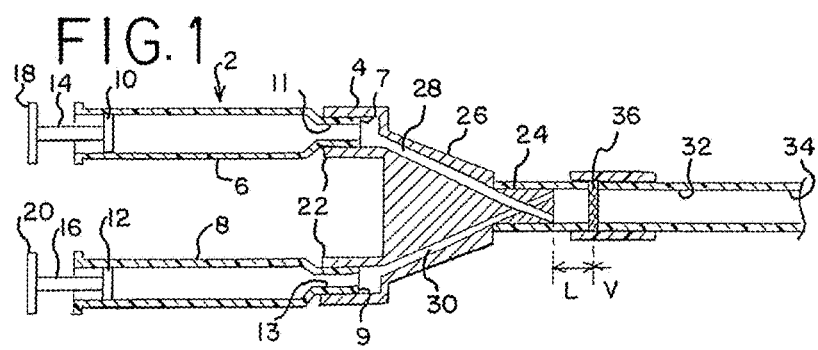
FIG. 1 is a partial cross-sectional view of one embodiment of a tissue sealant dispenser set forth in the present disclosure.
Figure 2:
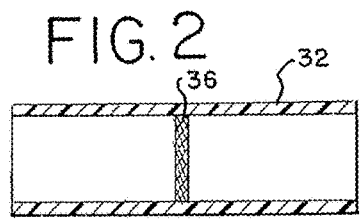
FIG. 2 is an enlarged cross-sectional view of the distal end portion of the dispenser of FIG. 1, showing portions of the dispenser removed.
Figure 3:
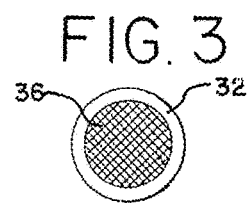
FIG. 3 is an enlarged distal end view of the distal end portion of FIG. 2.
Figure 4:
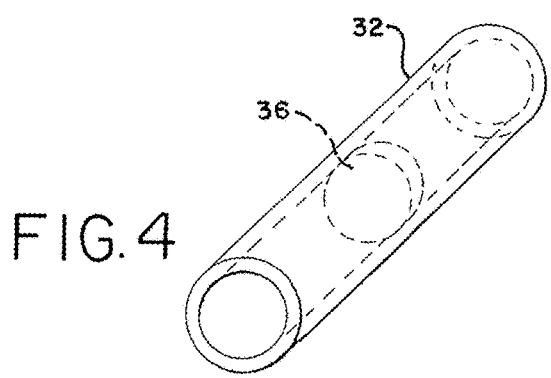
FIG. 4 is a perspective view of the distal end portion shown in FIG. 2.

In accordance with one embodiment of the present invention, FIG. 1 illustrates a dispenser, generally indicated at 2, for mixing at least two components of a combined fluid stream, such as a sealant, or tissue sealant or other combined fluid stream. Although the dispensers, systems and methods are generally illustrated and described in the context of a tissue sealant dispenser, it is understood that the present invention is not limited to such a dispenser or to the mixing of tissue sealant components, and that the present invention has applications in a variety of settings where mixing of component fluid streams is desired.

As shown in FIG. 1, dispenser 2 includes at least two fluid component sources, illustrated in the form of hollow cylinders or barrels 6 and 8, although other source containers from which fluid components are provided may be used. In the embodiment of FIG. 1, each barrel has a generally cylindrical interior or bore in which one of the fluid components such as fibrinogen or thrombin for forming fibrin tissue sealant is stored. The distal end 7, 9, respectively, of each barrel has an outlet port 11, 13, respectively, for communicating with a dispensing tip structure, generally at 4.

In FIG. 1, the bore of each barrel 6, 8 preferably slidably receives a piston or plunger 10, 12, respectively, for ejecting the sealant component from the respective bore. A plunger or pusher 14, 16 is associated with each piston and extends proximally from each respective bore. A thumb-rest 18, 20 is preferably associated with each plunger 14, 16 and may be actuated or pushed manually or automatically to eject the component. The thumb-rests 18, 20 may be actuated either independently or simultaneously, such as by a common actuator or yoke that couples the plungers together for simultaneous movement.

As shown in FIG. 1, the illustrated tip assembly or structure is a multi-part assembly and includes a flow director 26. The flow director 26 has a proximal end 22 and a distal end 24 and defines respective first and second passageways 28 and 30. Each passageway 28, 30 communicates with a respective bore of the barrels 6, 8 to allow the respective component to exit the distal end 24. As shown in FIG. 1, the inlet to each passageway 28 and 30 is suitable for attachment to one of the outlets from barrels to 6, 8 such as, for example, by a luer fitting or other attachments as will be apparent to persons of skill in the relevant field.

Although manually actuated plungers are illustrated for dispensing the fluid components, other types of devices may be used in connection with the present invention including manually or electrically actuated dispensers. Further, as noted above, it is contemplated that the present invention is not limited to dispensers for sealant and may be used to combine two or more components for other combined fluid streams for other applications within or outside of the medical field.

In FIG. 1, each of the first and second passageways 28, 30 communicates with one of the components as a separate fluid stream until such streams approach or are at the distal end 24. As shown in FIG. 1, the first and second passageways 28, 30 may be non-parallel and non-intersecting relative to one another such that they direct each component stream into a combined third passageway 32 at an angle that may assist combination of the two streams. For example, as shown in FIG. 1, the passageways are separate (with one passageway 28 or 30 being located offset and non-intersecting to the other) until the streams exit their respective passageways. In FIG. 1, the exiting streams are initially directed away from each other, towards opposed inner surfaces of the third passageway 32 which will deflect the separate stream and cause them to converge. The flow of the fluid component streams in the third passageway 32 downstream of the distal end 24 may be turbulent or otherwise provide fluid flow conditions which result in some mixing of the exiting streams of fluid components in this region.

Figure 5:
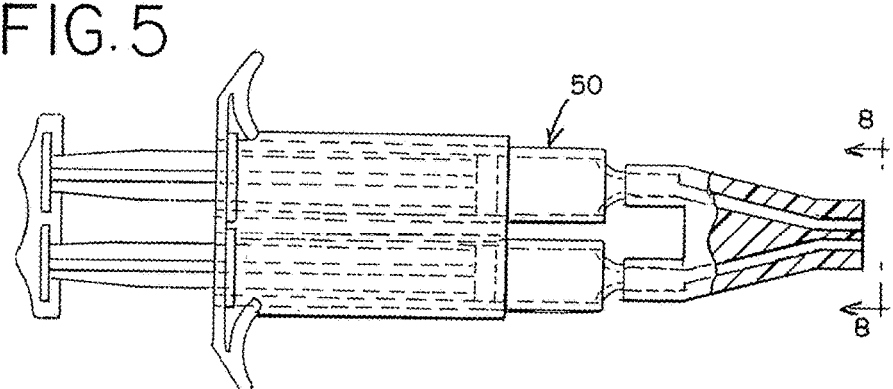
FIG. 5 is a top view of an alternative dispenser, similar to FIG. 1 with a mixing portion removed, showing portions in cross section to illustrate the fluid stream passageways defined in a distal end portion of the dispenser.
Figure 6:
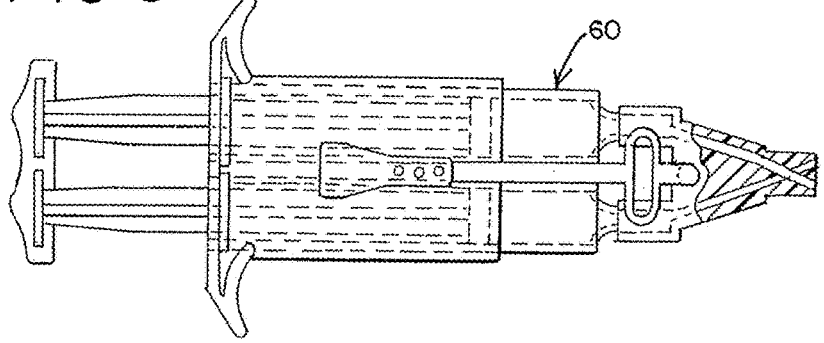
FIG. 6 is a top view of the dispenser of FIG. 1 with a mixing portion removed, showing portions in cross section to illustrate the fluid stream passageways defined in a distal end portion of the dispenser.
Figure 7:
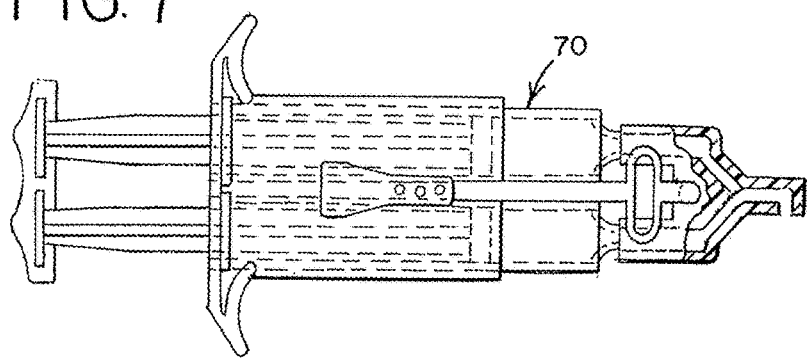
FIG. 7 is a top view of another alternative dispenser, similar to FIG. 1, with a mixing portion removed, showing portions in cross section to illustrate the fluid stream passageways defined in a distal end portion of the dispenser.
Figure 8:
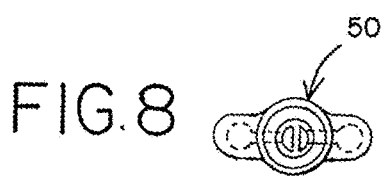
FIG. 8 is a distal end view of the dispenser of FIG. 5.
Figure 9:
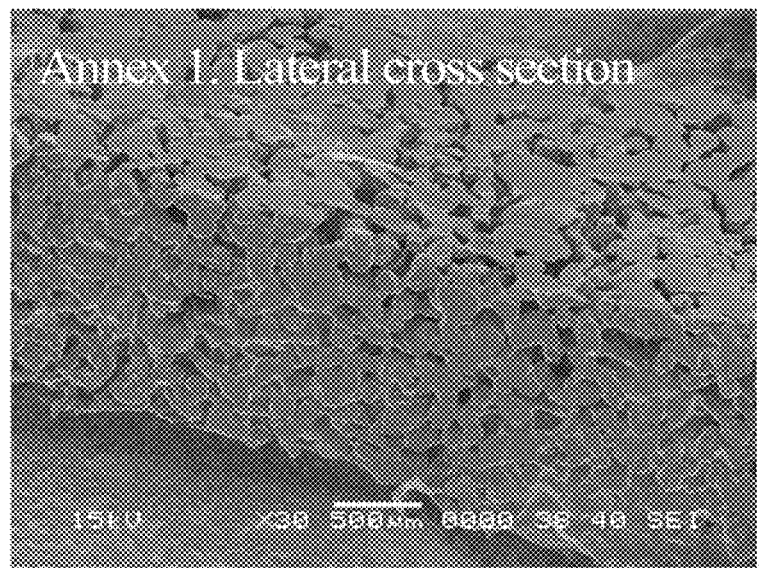
FIG. 9 is a scanning electron picture showing a lateral cross section of a sintered polypropylene material having a width of approximately 8.0 millimeters (mm) and a thickness of about 1.0 mm at about ×30 magnification.

In FIGS. 5-8, each figure includes an alternative orientation for the component passageways of the flow director, although other orientations may be used. The alternative dispensing devices 50, 60 and 70, respectively in FIGS. 5 and 8, show a straight and parallel orientation, where the fluid component streams exit the flow director along generally parallel paths. FIG. 6 shows non-parallel and non-intersecting flow paths similar to that of FIG. 1. FIG. 7 shows right-angled parallel flow paths at the distal end of the device (with one passageway located in front of the other and only one passageway being shown in FIG. 7). Other orientations are also possible.

As described above, and further shown in FIGS. 1-4, a third passageway 32 communicates with the first and second passageways 28, 30. A distal-most dispensing end 34 of the third passageway 32 provides for exiting of the mixed component stream and may include an orifice of any desired shape or a dispensing structure such as a tubing segment, cannula, spraying device, spray head or other types of dispensing devices, depending on the desired form in which the combined mixture is to be applied and/or the work surface.

In accordance with the present invention, a mixer, generally indicated at 36, is positioned upstream of the dispensing end 34 of the third passageway 32 for mixing of the component streams. As the component streams flow through the mixer 36, they are mixed together to provide a thorough mixing of two or more components to create a substantially homogeneous combined fluid stream that is dispensed from the dispensing end 34.

The mixer 36 described herein is preferably formed of a three-dimensional lattice or matrix that defines a plurality of tortuous interconnected passageways through the mixer. As a result of this structure, the component fluid streams are intimately mixed together as they pass through the mixer. The mixer 36 may provide for a laminar flow of the fluid component streams to enhance mixing between the fluid component streams, or otherwise provide fluid flow conditions which preferably promote significant mixing of the fluid component streams.

One preferred material for the mixer is illustrated in cross-sections in FIGS. 9-16. The material shown there is polymeric material formed by sintering to define an integral porous structure. The lattice or matrix of polymeric material forms a plurality of essentially randomly-shaped, tortuous interconnected passageways through the mixer. The material of the mixer 36 may be selected, for example, from one or more of the following: Polyethylene (PE), High Density Polyethylene (HDPE), Polypropylene (PP), Ultra High Molecular Weight Polyethylene (UHMWPE), Nylon, Polytetra Fluoro Ethylene (PTFE), PVdF, Polyester, Cyclic Olefin Copolymer (COC), Thermoplastic Elastomers (TPE) including EVA, Polyethyl Ether Ketone (PEEK), polymer materials other than polyethylene or polypropylene or other similar materials. The mixer 36 may also be made of a polymer material that contains an active powdered material such as carbon granules or calcium phosphate granules with absorbed molecules. Other types of materials are also possible. A sintered polypropylene material suitable for the present invention may be available from commercial sources, such as from Bio-Rad Laboratories, Richmond, Calif., United States, Porex Porous Products Group of Porex Manufacturing, Fairburn, Ga., United States, Porvair Technology, a Division of Porvair Filtration Group Ltd., of Wrexham, United Kingdom, including Porvair Vyon Porvent, PPF or PPHP materials, or Micro Pore Plastics, Inc., of 5357 Royal Woods, Parkway, Tucker, Ga. 30084, http://www.microporeplastics.com/.

Other materials that may be sintered to define an integral porous structure may include glasses, ceramics, and metals. In regard to metals, materials such as bronze, stainless steel, nickel, titanium, and related alloys may be used. Particular examples may include stainless steels, such as 316L, 304L, 310, 347, and 430, nickel alloys, such as HASTELLOY C-276, C-22, X, N, B, and B2 (HASTELLOY being a registered trademark of Haynes International, Inc. of Kokomo, Ind.), INCONEL 600, 625, 690, MONEL 400 (INCONEL and MONEL being registered trademarks of Huntington Alloys Corp of Huntington, W. Va.), Nickel 200 and Alloy 20, and titanium. Sintered metal materials suitable for use in the mixers and mixing methods of the present disclosure may be available from commercial sources, such as from Porvair Technology, a Division of Porvair Filtration Group Ltd., of Wrexham, United Kingdom (including BRM bronze materials) and Mott Corporation, of Farmington, Conn. (including stainless steels, nickel alloys (HASTEALLOY, INCONEL, MONEL, Nickel 200, Alloy 20) and titanium).

It is also possible that the mixer 36 may be made of one or more materials having one or more characteristics that may assist mixing of the component streams. By way of example and not limitation, the material may be hydrophilic, which is material that essentially absorbs or binds with water, hydrophobic, a material which is essentially incapable of dissolving in water, oleophobic, a material which is essentially resistance to absorption of oils and the like, and/or have other characteristics that may be desired to enhance mixing of the components.

As noted above, the mixer 36 preferably is made in whole or in part of a three-dimensional lattice or matrix that defines a plurality of tortuous, interconnecting passages therethrough. In FIGS. 9-16, the streams of the components may pass through the illustrated three-dimensional lattice or matrix that defines a plurality of tortuous, interconnecting passages so that the component streams are thoroughly mixed to create an essentially homogeneous combined fluid stream. At FIGS. 9-12, scanning electron pictures show lateral sections respectively at about ×30, ×100, ×350 and ×200 magnifications for a sintered polypropylene material having a width of approximately 8.0 millimeters (mm) and a thickness of about 1.0 mm. At FIGS. 13-16, scanning electron pictures show a longitudinal section respectively at about ×30, ×100, ×250 and ×350 magnifications for the same material shown in FIGS. 9-12, illustrating other views of the three-dimensional lattice. As shown in FIGS. 9-16, the illustrated passages preferably intersect at one or more random locations throughout the mixer such that the two component streams are randomly combined at such locations as such streams flow through the mixer. It should be understood that the three-dimensional lattice or matrix may be formed in a variety of ways and is not limited to the random structure of a sintered polymeric material as shown in FIGS. 9-16.

The illustrated mixer 36 in FIGS. 1-4 is made of a porous material and may have varying porosity depending on the application. Such porous material preferably has a porosity that allows the streams of the components to pass through to create a thoroughly-mixed combined fluid stream. The porosity of a material may be expressed as a percentage ratio of the void volume to the total volume of the material. The porosity of a material may be selected depending on several factors including but not limited to the material employed and its resistance to fluid flow (creation of excessive back pressure due to flow resistance should normally be avoided), the viscosity and other characteristics and number of mixing components employed, the quality of mixing that is desired, and the desired application and/or work surface. By way of example and not limitation, the porosity of a material that may be employed for mixing fibrin components may be between about 20% and 60%, preferably between about 20% to 50% and more preferably between about 20% and 40%.

Figure 17:
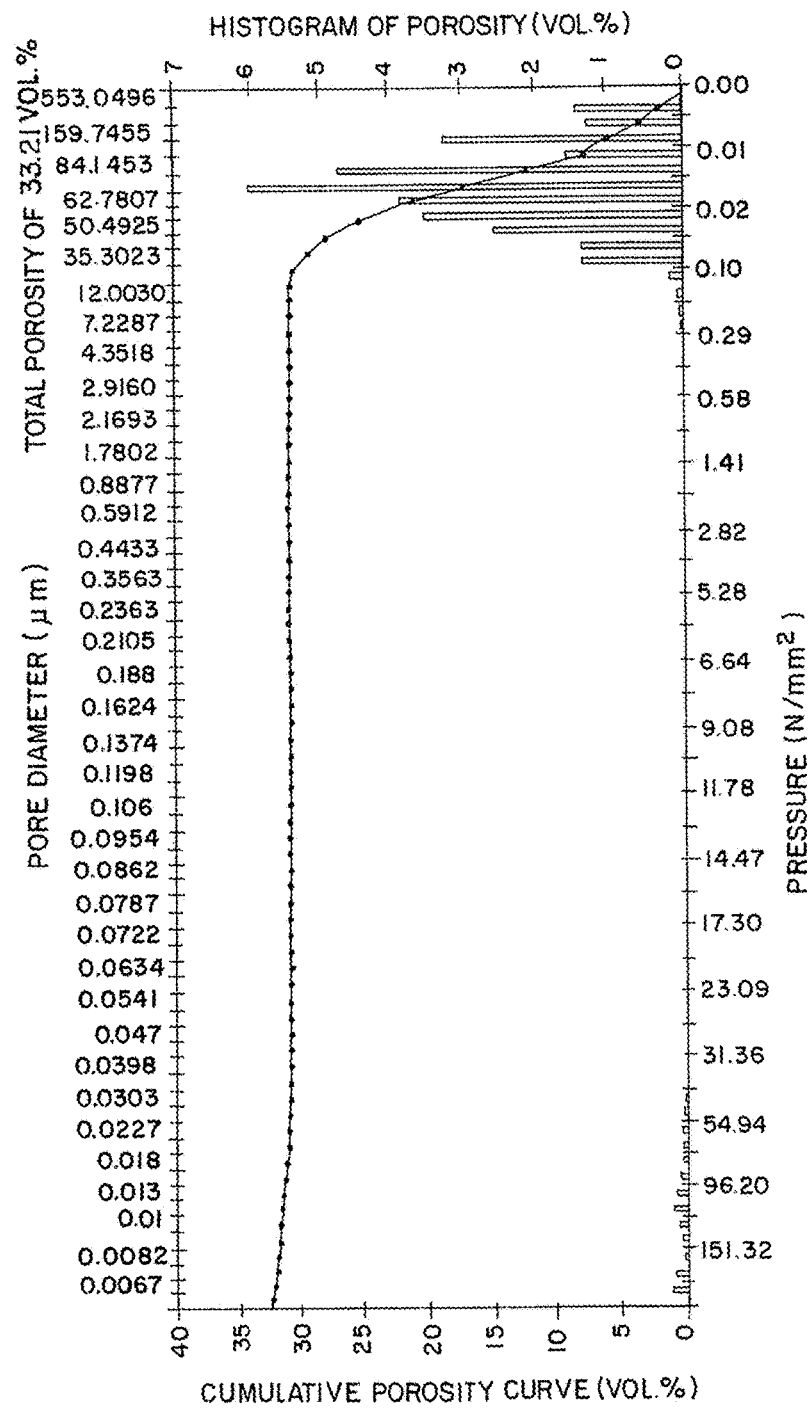
FIG. 17 shows porosity measurements of a selected material, of sintered polypropylene, obtained using a mercury porosity test.

At FIG. 17, porosity measurements of a selected material, manufactured by Bio-Rad Laboratories, are shown as obtained using a mercury porosity test on an Autopore 1111 apparatus, a product manufactured by Micromeritics of Norcross, Ga. It may also be possible to determine the porosity of a selected material in other ways or using other tests. At FIG. 17, such porosity measurements show the total volume of mercury intrusion into a material sample to provide a porosity of about 33%, an apparent density of about 0.66 and an average pore diameter of about 64.75 microns. Materials with other porosities also may be employed for mixing fibrin or for mixing combined fluid streams other than fibrin, as depending on the desired application.

Also, the mean pore size range of the mixer may vary. In the three-dimensional lattice shown in FIGS. 9-16, the mixer 36 may define a plurality a pores that define at least a portion of the flow paths through which the streams of the components flow. The range of mean pore sizes may be selected to avoid undue resistance to fluid flow of such component streams. Further, the mean pore size range may vary depending on several factors including those discussed above relative to porosity. Several mean pore size ranges for different materials for the mixer are shown in Table 1, except at no. 16 which includes a "control" example that lacks a mixer.

TABLE 1

PART III: Evaluation of single porous disks
Materials from Porvent and Porex

| Sample ID | Type | Form | Property | Mean Pore Size | Thickness | Mixing |
|---|---|---|---|---|---|---|
| 2 | | PE sheet | Hydrophobic | 5-55 μm | 2.0 mm | good |
| 21 | | PP sheet | Hydrophobic | 15->300 μm | 2.0 mm | good |
| 6 | | PE sheet | Hydrophobic | 20-60 μm | 3.0 mm | Good |
| 19 | | PP sheet | Hydrophobic | 70-210 μm | 1.5 mm | Good |
| 22 | | PP sheet | Hydrophobic | 70-140 μm | 3.0 mm | Good |
| 24 | | PP sheet | Hydrophobic | 125-175 μm | 3.0 mm | Good |
| 1 | | | Hydrophobic | 7-12 μm | 1.5 mm | no fibrin extrusion |
| 8 | | PE sheet | Hydrophobic | 40-90 μm | 1.5 mm | Good |
| 7 | | PE sheet | Hydrophobic | 20-60 μm | 1.5 mm | Good |
| 9 | | PE sheet | Hydrophobic | 20-60 μm | 3.0 mm | Good |
| 16 | | PE sheet | Hydrophobic | 40-100 μm | 1.5 mm | Good |
| 18 | | PE sheet | Hydrophobic | 40-100 μm | 3.0 mm | Good |
| 20 | | PE sheet | Hydrophobic | 80-130 μm | 3.0 mm | Good |
| 14 | | PE sheet | Hydrophobic | 20-60 μm | 1.5 mm | Good |
| 17 | | PE sheet | Hydrophobic | 80-130 μm | 1.5 mm | Good |
| 26 | Control | | | | | |
| 27 | | PP sheet | Hydrophobic | 7-145 μm | 1.5 mm | Good |

Table 1 includes several commercial sintered polyethylene (PE) or polypropylene (PP) materials manufactured by Porex or by Porvair under the tradename Porvent or Vyon. The table summarizes the mixing results achieved from each material based on quality of fibrin obtained after fibrinogen and thrombin (4 International Units (IU)/ml) passed through a device having a single mixer such as shown in FIG. 1, except for one experiment (at ID 26) which is the control and lacks any mixer. The indicated mean pore size ranges vary between about 5 and 300 microns. In Table 1, the ranges for materials nos. 2, 21, 6, 19, 22, 24, 8-9, 16, 18, 20, 14, 17, and 27 each generally indicate good mixing quality for fibrin. In Table 1, such mean pore size ranges are not intended to be exhaustive and other mean pore size ranges are also possible and useful for mixing. The mean pore size ranges indicated in Table 1 were obtained from the technical data sheets of the listed materials provided by the suppliers Porvair and Porex.

The mixer may be further configured and sized so as to provide sufficiently thorough mixing of the streams of the components. The size of the mixer may vary depending on such factors which include the size and/or configuration of the dispenser, the mixer porosity and mean pore size, the mixer material employed, the desired degree of mixing, the mixing components, and/or the desired application. For a mixer having the above discussed example ranges for porosity and mean pore sizes, the mixer thickness may range between about 1.5 mm and 3.0 mm, as indicated in Table 1. Other thicknesses are also possible including a variable or non-uniform thickness.

Also, the shape and configuration of the mixer may vary from the generally circular cross section or disk shape that is shown in FIGS. 1-4. It is possible that the mixer may have other shapes or configurations including but not limited to elliptical, oblong, quadrilateral or other shapes. In the embodiment shown in FIG. 1-4, the mixer radius may range between about 3 mm and 5 mm although other dimensions are also possible.

As shown in FIG. 1, the mixer 36 is preferably positioned downstream of the distal end 24, at about a length L from where the separate component streams are initially allowed to flow together, although it may also be positioned where the streams join. It is contemplated that the distance L may vary depending on the design requirements and extent of mixing that is required. By way of example, in a handheld dispenser of type shown in FIGS. 1-4 for use in fibrin delivery, the distance L may range between about 0 and 6 mm or more, preferably, between about 1 and 6 mm. Generally speaking, the homogeneity of fibrin created by the illustrated mixer decreases with a decrease in the distance L, such as 4 mm and less by employing the dispenser type shown in FIGS. 1-4. More preferably, a distance L of between about 5 and 6 mm is preferred for the embodiment shown in FIG. 1-4 although other distances are also possible. It is contemplated that other designs may be employed than the described Y-shaped passageway structure that is shown and/or other physical parameters may be employed for such structure such as, other diameters, lengths, number of passageways and/or passageway orientations, such as shown in FIGS. 5-8, so that the value of distance L may have a different range than described above and is not limited to the above ranges.

Also, the mixer may be manufactured in various ways which may depend on the desired shape, thickness and/or other characteristics of the material or materials that is employed for the mixer. By way of example and not limitation, the mixer may be fabricated or sectioned from one or more pieces of material having a desired size, thickness and/or other characteristics for the mixer. Alternatively, the mixer may be prefabricated including one or more molding processes to form a mixer having a desired size, thickness and/or other characteristics. It is also possible that the mixer may be manufactured in other ways. The mixer may be preassembled as part of a cannula, needle of the cannula, luer, spray tip, tube, or other device, such as by molding ultrasonic welding, mechanical fittings or other attachment techniques. By way of example and not limitation, FIG. 18 shows a mixer 80, similar to the mixer 36 of FIG. 1 that is located within a cannula-type device 82. Alternatively, the mixer may be assembled by the user as part of a suitable device prior to use although other uses may also be employed.

The material for the mixer may be characterized and selected for a given application based on one or more physical characteristics so as to provide a sufficiently and relatively homogeneous combined fluid stream downstream of the mixer and upon passing the component streams through the mixer. By way of example, Table 2 illustrates various sintered polymer materials for the mixers suitable for use in the dispensers systems and methods described herein, and their physical characteristics. The specific materials identified in Table 2 are manufactured by, for example, Porvair Filtration Group Ltd. (Hampshire, United Kingdom) or Porex Corporation (Fairburn, Ga., USA). The data represented in this table includes the K value from Darcy's Law, as indicated in the following equation:

$$Q=(K*S*\Delta P)/(\eta*L)$$

where Q is the Flow rate of fluid flow through the material;

S is the surface area of the material;

$\Delta P$ is the change in pressure between the upstream and downstream locations of the material;

L is the thickness of the material; and $\eta$ is the viscosity of the fluid flowing through the material, or if more than one fluid is flowing the viscosity of the more viscous component.

The K values typically represent a permeability value and are represented in Table 2 based on increasing K value, expressed in units of $\mu m^2 s$ which represents increasing values of permeability. Table 2 also summarizes several physical characteristics of the material including the relative values for minimum pore size (min.) mean flow pore size, maximum pore size (max.), average bubble point (or pressure that causes the liquid to create air bubbles), thickness, and porosity. The physical characteristics of each of the materials in Table 2 were obtained based on testing using methods known to those of skill in the art.

By way of example and not limitation, the K values in Table 2 were obtained by permeability testing using water passed through the listed materials having the indicated physical characteristics. The permeability test was helpful to characterize materials based on their K value and, these materials are listed in order of increasing K value in Table 2. For the measurement of permeability, the materials employed included sintered porous material sheet supplied by Porvair and Porex. The permeability test was performed on a syringe that was filled with water. The pressure reducer was turned off and all connections downstream of the syringe were opened. Then water was allowed to flow through the syringe until the pressure drop between top and bottom of the syringe was about zero. The pressure reducer was then switched on and compressed air was injected to push water from the syringe at a constant flow rate. The volume of injected air was determined based on monitoring the flow of water between upper and lower volumetric markings on the syringe. As soon as the water meniscus crossed the upper mark, the time and pressure were recorded (P1). When the water meniscus crossed the lower mark on the syringe body, the total time (t), pressure (P2) and volume of water (V) were recorded. In addition to the known values of P1, P2, t and V, the remaining parameters for the calculation of permeability that were known include: Diameter of sintered material disc is about 10 mm, the thickness is about 1.5 mm, the surface of sintered material disc is about 78.54 $mm^2$, the Dynamic viscosity of water $10^{-3}$ Pascal second (Pa·s). This test was used to determine the K values in Table 2.

As described herein, it is contemplated that other liquids, gases and solids may be used to determine a K value from Darcy's Law for these materials or other materials. It is realized that different liquids, gases and solids will change the viscosity value ($\eta$) of Darcy's Law and, as such, will provide different K values or ranges for a given set of physical properties (thickness L and surface area S) of the material, flow rate Q and pressure difference $\Delta P$ that may be employed. Further, even where the same liquid, gas or solid is used, such that the viscosity is held constant, other parameters may be varied to achieve different K values. By way of example and not limitation, any one or more of the flow rate, surface area, thickness, and/or pressure difference may be varied and, as such, vary the resulting K value that is determined.

Figure 64:
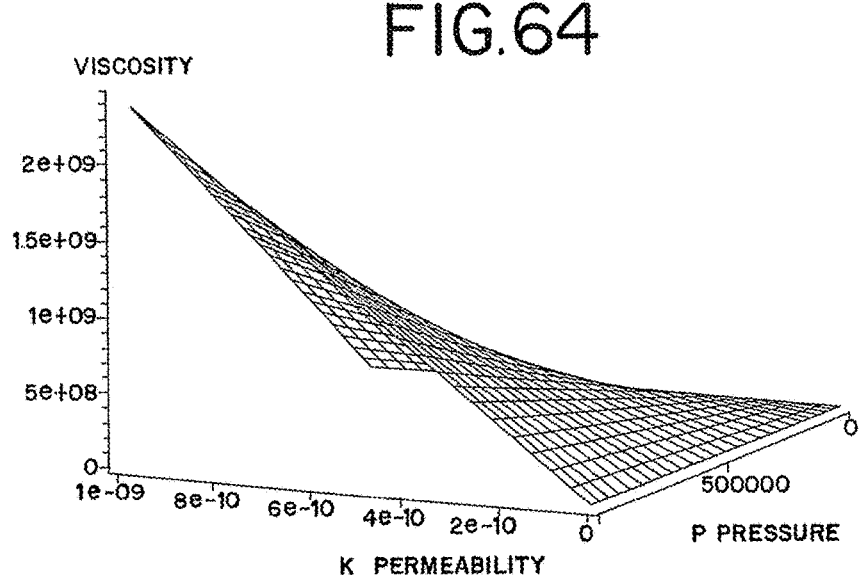
FIGS. 64-65 are graphs showing a plot of permeability K values, pressure values and viscosity values relative to one another, based on Darcy's Law, with the remaining variable being held constant.
Figure 65:
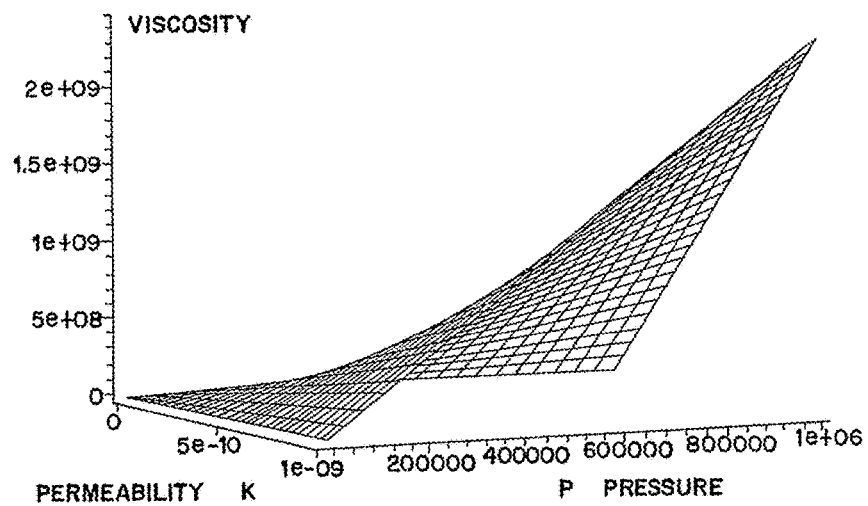

Turning briefly to FIGS. 64-65, a three-dimensional curve shows the permeability or K values along one axis, pressure values along a second axis and viscosity values along a third axis (with FIG. 65 identical to FIG. 64, except the axes of permeability and pressure have been rotated clockwise to better show the curve). Generally speaking, the illustrated curve is applicable to any liquid, gas or solid that may be employed for permeability testing of a given material. By way of

TABLE 2

| | Permeability | | Porosity | | | | |
|---|---|---|---|---|---|---|---|
| Sample | K "μm" | Min. | Mean Flow Pore | Max | Avg. Bubble Pt. | Thick | Porosity |
| 1 | 0.55 | 3 | 5 | 7 | 13 | 1.5 | 45 |
| 2 | 1.41 | 4.0-7.0 | 17-22 | 50-60 | 50-70 | 2 | 27 |
| 3 | 1.93 | 5.0-8.0 | 8.0-12 | 12.0-18.0 | 15-25 | 2 | 44 |
| 4 | 3.41 | 4.0-7.0 | 17-22 | 50-60 | 50-70 | 2 | 27 |
| 5 | 3.76 | 4.0-7.0 | 17-22 | 50-60 | 50-70 | 2 | 27 |
| 6 | 4.72 | 6 | 16 | 36 | 47 | 3 | 42 |
| 7 | 5.08 | 9 | 23 | 49 | 57 | 1.5 | 48 |
| 8 | 5.81 | 10 | 36 | 88 | 101 | 1.5 | 39 |
| 9 | 6.18 | 7 | 21 | 45 | 52 | 3 | 45 |
| 10 | 6.48 | 6.0-9.0 | 35-45 | 130-160 | 101-130 | 1.5 | 39 |
| 11 | 6.55 | 6.0-9.0 | 35-45 | 130-160 | 101-130 | 1.5 | 39 |
| 12 | 6.67 | 7.0-11 | 30-40 | 85-105 | 60-80 | 1.68 | 39 |
| 13 | 7.14 | 6.0-9.0 | 35-45 | 130-160 | 101-130 | 1.5 | 39 |
| 14 | 7.14 | 9 | 28 | 64 | 67 | 1.5 | 49 |
| 15 | 7.32 | 7.0-11 | 25-35 | 68-88 | 55-75 | 2 | 35 |
| 16 | 7.89 | 14 | 43 | 119 | 108 | 1.5 | 51 |
| 17 | 10.90 | 13 | 65 | 300 | 183 | 1.5 | 56 |
| 18 | 10.99 | 9 | 32 | 70 | 85 | 3 | 46 |
| 19 | 12.30 | 11 | 80 | 300 | 207 | 1.5 | 50 |
| 20 | 12.57 | 10 | 51 | 140 | 129 | 3 | 48 |
| 21 | 14.09 | 13-17 | 80-100 | 300 | 180-210 | 2 | 51 |
| 22 | 15.02 | 10 | 61 | 217 | 163 | 3 | 46 |
| 23 | 15.64 | | | | | | |
| 24 | 16.49 | 12 | 81 | 300 | 227 | 1.5 | 42 |
| 25 | 25.23 | 15 | 298 | 300 | TP | 3 | 49 | example, FIGS. 64-65 show the variation in permeability or K values, pressure values and viscosity, assuming other parameters of Darcy's Law, such as surface area S, flow rate Q and material thickness L are held constant. As indicated in FIGS. 64-65, for a given viscosity and pressure value, the permeability or K value may known according to the illustrated curve. Even if only one of the permeability, pressure or viscosity value is constant, the curve provides an indication of the other two values, which may vary along the illustrated curve, due to their relationship to each other based on Darcy's Law, described above.

TABLE 3

| Sample | MFP * thick * PV * 1000 | K |
|---|---|---|
| 1 | 3.375 | 0.55 |
| 3 | 8.8 | 1.93 |
| 2 | 10.53 | 1.41 |
| 4 | 10.53 | 3.41 |
| 5 | 10.53 | 3.76 |
| 7 | 16.56 | 5.08 |
| 6 | 20.16 | 4.72 |
| 14 | 20.58 | 7.14 |
| 15 | 21 | 7.32 |
| 8 | 21.06 | 5.81 |
| 12 | 22.932 | 6.67 |
| 10 | 23.4 | 6.48 |
| 11 | 23.4 | 6.55 |
| 13 | 23.4 | 7.14 |
| 9 | 28.35 | 6.18 |
| 16 | 32.895 | 7.89 |
| 18 | 44.16 | 10.99 |
| 24 | 51.03 | 16.49 |
| 17 | 54.6 | 10.9 |
| 19 | 60 | 12.3 |
| 20 | 73.44 | 12.57 |
| 22 | 84.18 | 15.02 |
| 21 | 91.8 | 14.09 |
| 25 | 438.06 | 25.23 |

At Table 3, the K values of the materials listed at Table are represented. By way of example and not limitation, good, homogeneous mixing of a combined fibrinogen and thrombin mixture has been observed using mixer or disk made of a material having a K value from Tables 2-3 between approximately 5 and 17. In addition, Table 3 includes a numerical product of the mean flow pore size (MFP), thickness and porosity volume (PV) multiplied by 1000 (based on increasing value of this product). It has also been observed that using a mixer having a MFP*thickness*PV*1000 value, within the range of about 16 to 55 achieves good, homogeneous mixing of fibrin. The mixer material may also be selected based on one or more of the above physical characteristics or other characteristics. As discussed above, the permeability or K values may vary from those discussed above in Tables 2-3, for example, where a liquid other than water is used, or where a gas and solid may be employed for the permeability testing or where different physical characteristics or parameters are employed. In such instances, it is contemplated that an appropriate range of K values will be determined and the material of the mixer may be appropriately selected based on a range of K values that is determined to provide sufficient quality of mixing. Also the K values may differ due to the technique utilized in measuring the value.

Additionally, three commercial sintered bronze materials manufactured by Porvair under the tradename BRM have been tested using methods known to those of skill in the art to develop physical characteristic data similar to that presented in Tables 2 and 3. Bronze materials are believed to be better suited for higher flow rate (for example, on the order of one liter/second), higher pressure (for example, in excess of 1 Bar) applications, such as may occur in industrial processes. BRM 30 has a range of pore sizes from 9 μm to 135 μm, BRM 40 has a range of pore sizes from 12 μm to 300 μm, and BRM 60 has a range of pore sizes from 20 μm to above 300 μm. The mean flow pore sizes are 38 μm, 58 μm, and 100 μm for the BRM 30, BRM 40, and BRM 60 materials, respectively. Furthermore, the K values for these materials were 26.99, 46.19, and 65.94 for the BRM 30, BRM 40 and BRM 60 materials, respectively. While all three materials exhibit generally good mixing properties, the BRM 60 material has been used in the examples below.

FIGS. 19-21 illustrate another embodiment of the present invention which includes a tissue sealant dispenser, generally indicated at 102. Similar to the dispenser 2 shown in FIGS. 1-4, the dispenser 102 in FIGS. 19-21 includes a pair of hollow barrel or tubes 106, 108, pistons 110, 112, plungers 114, 116 and thumb rests 118, 120, and flow director 126. The flow director 124 has a distal end 124, and first, second and third passageways 128, 130 and 132. As shown in FIG. 21, the respective openings A, B of the first and second passageways 128, 130 are positioned so as to assist combination of the two separate streams as they exit the distal end 124, as described above. More specifically, in FIGS. 19-21, the outlets are located in offset relationship and direct fluid flow outwardly toward the wall of tubing 132, although other locations and/or orientations may be used.

Referring to FIG. 19, the dispenser preferably has two or more mixers for enhanced mixing and preferably two, or first and second mixers 136A and 136B. In FIG. 19, such mixers 136A and 1368 are located upstream of a dispensing end 134 and in spaced-apart series relationship, spaced from each other at a distance V along the passageway 132. Generally speaking, the homogeneity or quality of mixing of fibrin increases with an increase in the number of mixers, such as for two mixers, although any number of mixer may be used.

The passageway 132 may be of one-piece construction or comprised of separate portions or tubing segments 132A, 132B and 132C, with the mixers 136A, 136B located between the segments 132A, 132B and 132C, as shown in FIG. 19, so as to ensure the desired spacing between the mixers 136A, 136B, between the upstream mixer 136A and the distal end 124, and between the downstream mixer 136B and the dispensing end 134. An outer housing 138 may be sized to tightly overfit the tubing segments 132A, 132B and 132C and the mixers 136A and 136B for supporting and aligning the mixers 136A, 136B and tubing segments 132A, 132B, 132C.

The distance V between the mixers 136A, 136B may be varied between about 0 mm, in which the mixers are adjacent to each other, and 6 mm or more. FIGS. 22-27 illustrates some different possible spacing distances between the mixers 136A, 136B. The distance V between two mixers 136A, 136B is shown at about 0 mm, 1 mm, 2 mm, 3 mm, 4 mm and 5 mm (as respectively indicated by FIGS. 22-27). Generally speaking, when employed in a tissue sealant application, it has been found that the presence of fibrin between the two mixers increases when the distance V between them increases. A distance V of about 3 mm and above in the illustrated embodiment has resulted in good fibrin formation to form a combined fluid stream having sufficient homogeneity. As discussed above, the length L upstream of the first mixer may also be selected between about 0 mm to 6 mm or more. For example, if two mixers are used having the above discussed size range, one combination may include a distance V between the mixers 136A, 136B of about 4 mm or less and a length L between the upstream mixer 136A and the distal end 124 of about 6 mm or less, so as to minimize fibrin formation on either side of the mixers 136A, 136B and/or clogging of the pores of the mixers 136A, 136B. Other variations or combinations of distances V and lengths L are also possible. As previously discussed above for the value L, the value V may also vary based on different designs and/or the different parameters that are employed in such design and so the value V is not limited to the above discussed values or ranges.

The mixing and dispensing systems described herein may provide for a "Stop and Go" device or process, in which the flow of fluid component streams are intermittently started and stopped. For such "Stop and Go" device or process, the length L and/or the distance V preferably should not generate significant fibrin formation on the mixer or mixers or between the mixers if more than one mixer is employed. For a "Stop and Go" device employing at least two mixers, the length L and the distance V may vary. By way of example and not limitation, for a two mixer device, a length L of about 3 mm and a distance V of about 4 mm may achieve sufficiently thorough mixing as well as avoid significant generation of fibrin on or between the two mixers. Other variations of the length L and the distance V are also possible from those discussed and may be employed, depending on the desired application and/or other designs and parameters that may be employed.

FIGS. 28-29, show two mixers, with a distance V at about 2 mm and 3 mm, respectively, therebetween, and a length L at about 6 mm. Any reasonable number of mixers is also possible to enhance mixing provided flow is not unduly restricted. Also FIGS. 30-32, respectively show mixer arrangements with one mixer 136A, two mixers 136A and 136B and three mixers 136A, 136B and 136C without any distance or spacing (V) therebetween and with a length L of about 6 mm. Where more than one mixer is used, the mixers do not have to have the same characteristics, such as porosity, mean pore size or length as describe above. It may be desirable to varying the characteristics of the mixers to increase the thoroughness of mixing as the fluid streams pass through the dispenser.

In FIG. 33, a further embodiment of the present invention includes a dispenser, generally indicated at 202. Similar to previously described embodiments, the dispenser 202 includes a pair of hollow barrels or tubes 206, 208, pistons 210 and 212, plungers 214 and 216, thumb rests 218, 220 and a flow director 226. A proximal end 222 of the dispenser 202 provides a common actuator, which joins the proximal ends of the plungers 214 and 216 together at the end 222, for simultaneously ejecting the components from a distal end 224. The distal end 224 defines separate passageways 228 and 230 for separately ejecting the respective components into a third passageway 232 in which a single mixer 236 is located upstream of a dispensing end 234 and is positioned downstream of the distal end 224 at a length L. As noted above, other variations are possible including variations in the number of mixers and the length L.

Figure 10:
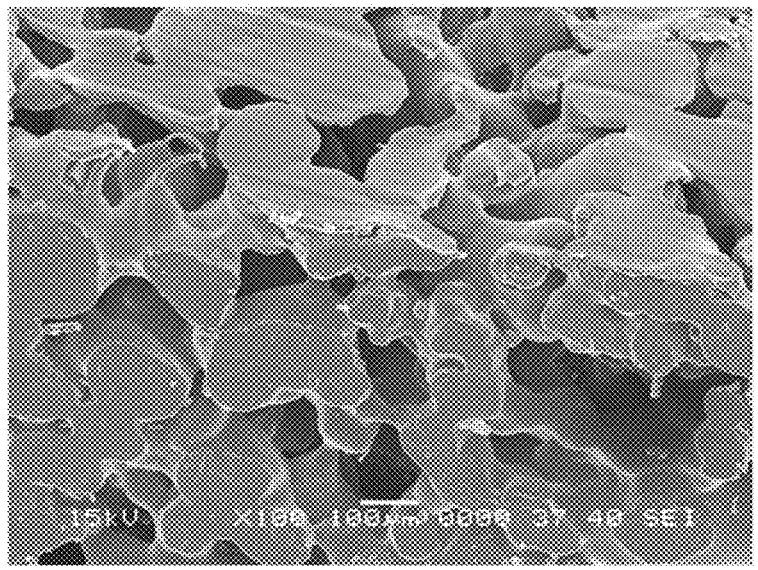
FIG. 10 is a scanning electron picture showing a lateral cross section of a sintered polypropylene material having a width of approximately 8.0 millimeters (mm) and a thickness of about 1.0 mm at about ×100 magnification.
Figure 11:
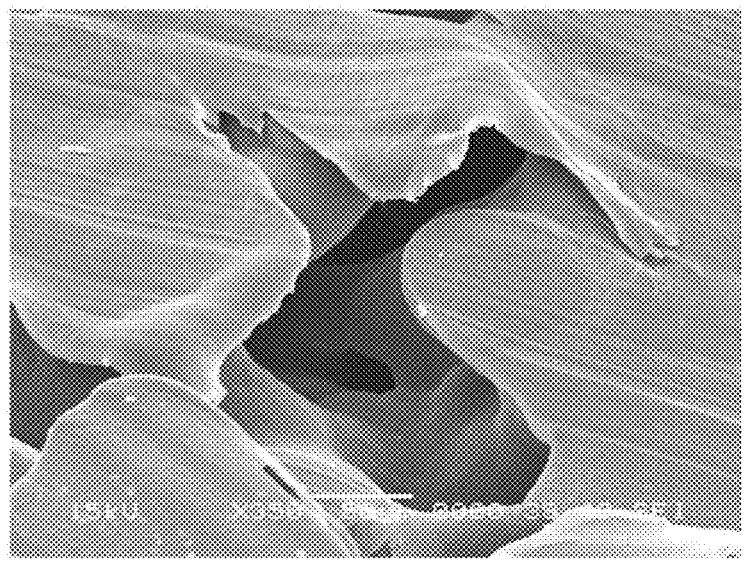
FIG. 11 is a scanning electron picture showing a lateral cross section of a sintered polypropylene material having a width of approximately 8.0 millimeters (mm) and a thickness of about 1.0 mm at about ×350 magnification.
Figure 12:
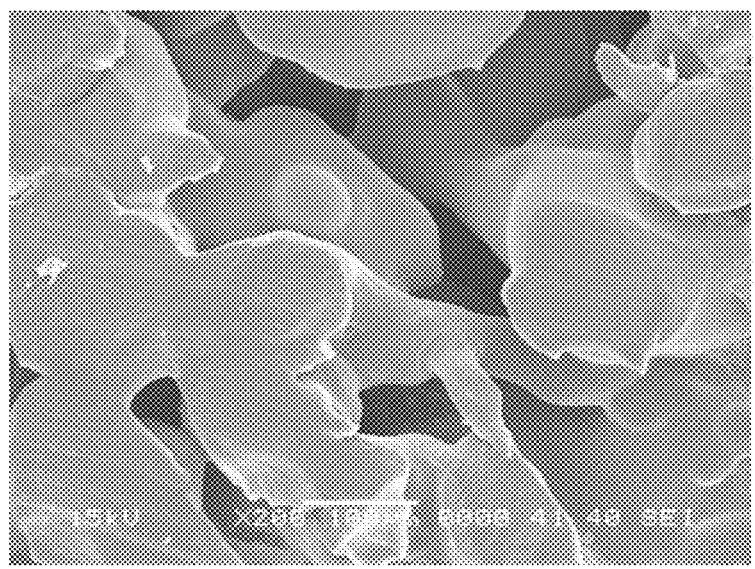
FIG. 12 is a scanning electron picture showing a lateral cross section of a sintered polypropylene material having a width of approximately 8.0 millimeters (mm) and a thickness of about 1.0 mm at about ×200 magnification.
Figure 13:
FIG. 13 is a scanning electron picture showing a longitudinal cross section of a sintered polypropylene material having a width of approximately 8.0 millimeters (mm) and a thickness of about 1.0 mm at about ×30 magnification.
Figure 14:
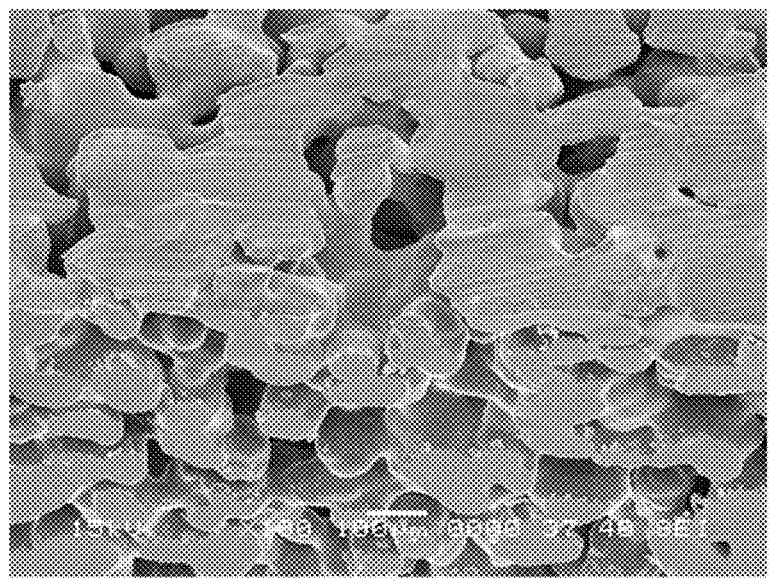
FIG. 14 is a scanning electron picture showing a longitudinal cross section of a sintered polypropylene material having a width of approximately 8.0 millimeters (mm) and a thickness of about 1.0 mm at about ×100 magnification.
Figure 15:
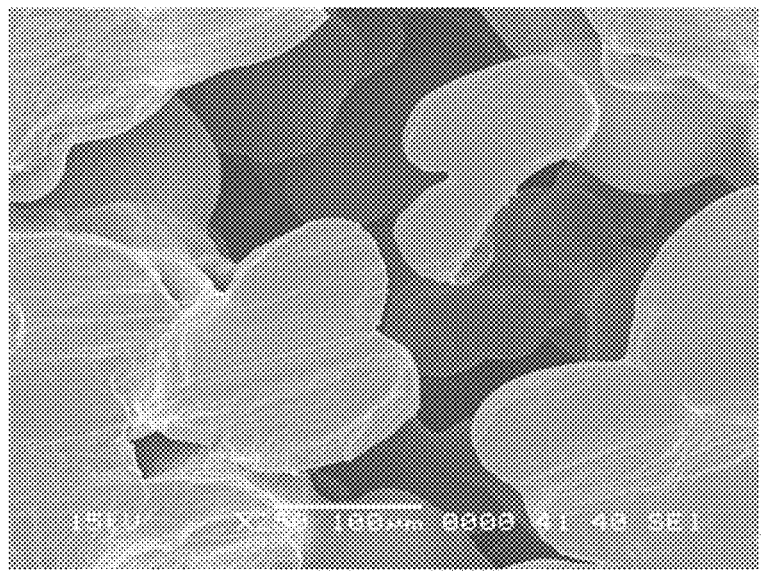
FIG. 15 is a scanning electron picture showing a longitudinal cross section of a sintered polypropylene material having a width of approximately 8.0 millimeters (mm) and a thickness of about 1.0 mm at about ×250 magnification.
Figure 16:
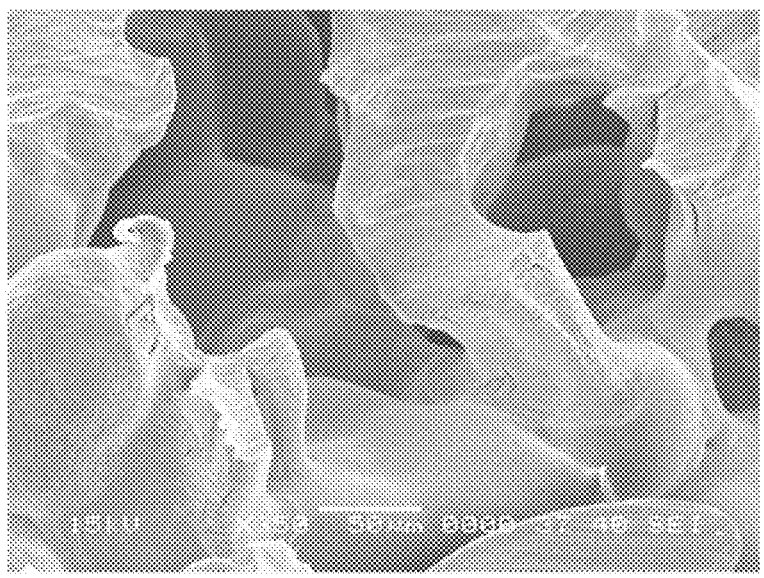
FIG. 16 is a scanning electron picture showing a longitudinal cross section of a sintered polypropylene material having a width of approximately 8.0 millimeters (mm) and a thickness of about 1.0 mm at about ×350 magnification.

In FIG. 33, a fourth passageway 240 is defined in the distal end 224 and is adapted for fluid communication with a source of sterile gas, such as air which communicates with the distal end via tubing (such as tubing as shown in FIG. 10 at 342). The source of gas may be actuated by pneumatic, mechanical, electrical and/or some combination thereof, such as described and shown in U.S. patent application Ser. No. 11/331,243 filed Jan. 12, 2006, which is incorporated herein by reference.

In FIG. 33, such dispenser 202 operates similarly to the dispenser 2 as described in FIGS. 1-4 except that the two components may be ejected from the device with the assistance of gas to provide a mixed gas and component fluid stream from the distal end 234 of the dispenser 202. It is also possible for the passageway 240 to introduce gas or water for cleaning the passageways of the mixer and/or the dispensing end 234 and/or other tubing or cannula structures located downstream, which may facilitate operation of a stop & go device during intermittent starting and stopping of fluid flow.

In FIG. 34, a modified dispenser, generally indicated at 302, includes identical parts as discussed above with respect to FIG. 33, except that the third passageway 332 includes two mixing devices 336A, 336B positioned in spaced-apart series upstream of a dispensing end 334. In accordance with aspects of the invention previously described, variations are possible for a length L between the upstream mixer 336A and the distal end 324 and a distance V between the upstream and downstream mixers 336A and 336B.

Other modifications are also possible. For example, the gas-assisted spray dispensers shown in FIGS. 33-34, or any of the above embodiments, may be modified to include various alternative orientations for the component passageways, such as and not limited to the orientations shown in FIGS. 5-8. For example, a modified dispenser may provide parallel component passageways for separate components fluid streams, such as using a catheter or other similar structure, having a desired length, such as for use as part of a laparoscopic spray device or other minimally invasive surgical instrument and/or procedure. If gas-assist is employed, the gas fluid stream may be located either upstream or downstream of the mixer, and/or upstream or downstream of the location where the fluid component stream are joined. Other variations from the above discussed modifications are also possible.

FIGS. 35-36 shows another dispenser, generally indicated at 402, which includes similar parts as discussed above with respect to FIG. 1, 19, 33 or 34 except that the device may employ a spray head 438, which includes a mechanical break up unit known as MBU that allows the components (such as fibrinogen and thrombin), to be sprayed with air and/or water and which is shown and described in U.S. Pat. No. 6,835,186, which is incorporated by reference herein. As discussed above with respect to other embodiments, the connector 438 in FIG. 35 may employ one or more mixing devices 436 located in the passageway 432 in which the fibrinogen or thrombin are combined. The air and/or water may be introduced into the combined stream either upstream or downstream of such mixing.

In accordance with another aspect of the present invention, FIGS. 37-40 show a connector, generally indicated at 500, that includes a mixing device 502 located therein. In FIG. 37, the connector 500 may be located in fluid communication with a dispensing device, such as a single or multi-barrel dispensing device, as previously described herein although other devices are also possible. As shown in FIG. 37, the connector is provided at the distal end of a collecting/dispensing device 504 having a single container, which device may, for example, be located downstream of the dispensing device in FIGS. 1-4 for storing or collecting the sufficiently mixed components after they have passed through the mixer. Other arrangements are also possible and are not limited to the devices shown and described.

As indicated in previous embodiments, the mixing devices 502 may be located in spaced relation to each other and located in series. The connector 500 also includes first and second ends, 506 and 508, respectively, which, as shown in FIGS. 39-40, may be respectively associated with a male and/or female luer locking feature for connection to the dispensing device 504, as shown, and/or other dispensing devices. In FIGS. 39-40, the connector in 500 includes a sleeve 510 which defines a fluid passageway 512 defined therein that receives the mixing devices. The sleeve 510 may include grooves 514 defined on the interior surface of the sleeve to receive a portion of an extension 516 that defines a channel or tubing in fluid communication with the device 504. The grooves may, for example, receive projections 518 defined in the extension 516 which may be inserted by rotating the projections along the curved profile of the grooves 514 (as shown in FIG. 514) to provide a luer lock type connection. It is possible that either end of the connector 500 may provide other shapes, configurations and/or types of connections that may prevent inadvertent disconnect of the fluid passageways, as may be desired, and, as such, are not limited to the connections shown and described.

FIGS. 41 and 42 show an alternate connector 600 having a single mixing device 602 located in a fluid passageway 604 defined in the connector 600. The connector 600 includes first and second ends 606 and 608, respectively, which may provide two female luer locks that may be attached to a dispensing device, such as a syringe or other device at each side of the connector.

FIGS. 43-46 show yet another modified connector 700, which employs two mixing devices 702 that are positioned in series within a fluid passageway 704 defined in the connector. As shown in FIG. 44, the connector 700 includes a first and second ends 706 and 708, which may respectively be associated with a female and male luer locking feature. The connector may be comprised of one or more tubing sections 710, 712, and 714, as shown in FIG. 44-46, which are attached together, for example, by mechanical connection or by ultrasonic welding. For example, the interior surface of the tubing section 710 includes a lock system to attach to the tubing section 706 and a respective end 714 of the tubing section 710 may allow for a locking connection between the tubing section 706 with a cannula, needle, syringe or other device. Generally speaking, it is preferred for the connector to have a luer lock feature where employed in medical applications although other connections are possible for other applications.

In accordance with a further aspect of the present invention, a method provides for mixing at least two separate streams of components, such as for example, sealant components. The method may be performed by providing a mixer such as at least one mixer 36, 236 or more than one mixer 136A, 136B, 336A, 336B, which includes a three-dimensional lattice or matrix that defines a plurality of tortuous, interconnecting passages therethrough, such as in any of the above-described embodiments. The method further provides for passing the at least two separate streams of components such as sealant components through the mixer.

As noted above, the method may be performed with at least one mixer or a plurality of mixers, such as two or more mixers positioned in series, either adjacent or spaced from one another. The method may also be repeated a plurality of times such that the flow of the two streams may be stopped and then the flow of the streams may be restarted so that the streams pass through the mixer with minimal clogging of such mixer.

During operation of the dispensers 2, 102, 202, 302, 402 in FIGS. 1-21, 33-35 two separate streams flow through the respective first and second passageways 28, 30, 128, 130, 228, 230 (only one passageway 330 being shown in FIG. 34) to the third passageway 32, 132, 232, 332, 432. As the streams flow through the three-dimensional lattice that defines the tortuous, interconnecting passages in the single mixer 36, 236, 436 or the mixers in series 136A, 136B, 336A, 336B the streams are mixed into an essentially homogeneous combined fluid stream.

By way of example, FIG. 47 shows a method for providing mixing of at least two separate components employing a connector 800, such as any of those described above having at least one mixer, which connector may be attached at one end to a device 802 having two separate containers 806 and 808, respectively, and attached at its other end to a dispenser 804. As noted above, the components may be allowed to flow from the separate containers 806 and 808 through corresponding separate passageways 810 and 812 to a combined passageway 814 which extends to the connector 800. The mixture of the components flows through the connector 800 having at least mixer positioned therein to a passageway 816 of the dispenser attached to the opposite side of the connector 800 for dispensing as desired.

Figure 48:
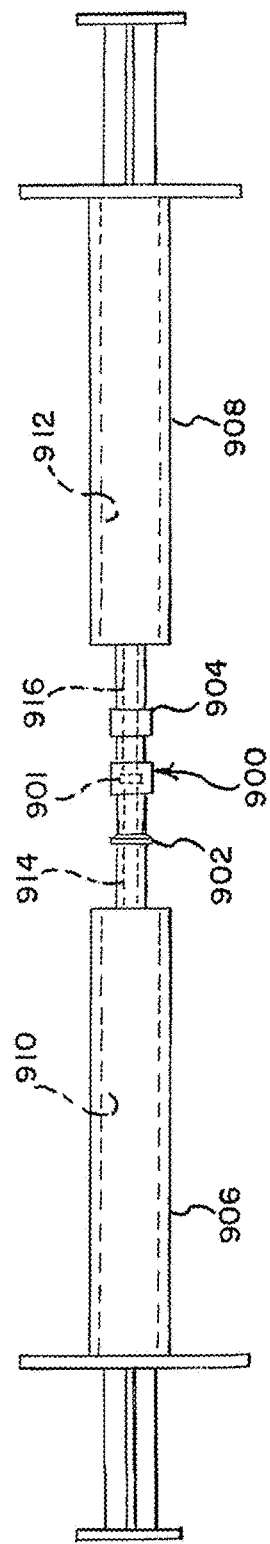
FIG. 48 is a top view of an alternate arrangement that includes two dispensing devices connected by one of the mixing devices shown in FIGS. 39-46.

Turning to FIG. 48, another embodiment of a mixing/dispensing system is shown. As seen in FIG. 48, a mixing device 900 is located between two containers, (e.g., dispensers) each holding a fluid (liquid or gas). The portion of the combined device that holds mixing device 900 can be integrated with one of the dispensers or be a connector, with at least one mixer 901 located therein. Such connector is shown having first and second ends 902 and 904, each connected to a dispenser 906 and 908, respectively, having a single container 910 and 912. By way of example and not limitation, the present invention provides a method for mixing at least two separate streams of fluid components, where each component, is separately located in one of the dispensers 906 and 908. Each container includes a distal passageway 914 and 916, respectively, which each fluidly communicate with one side of the mixing device 900, which as shown in FIG. 48 provide two female luer attachments, although the mixing device 900 may also be provided with two male luers on its ends 902 and 904 and/or some combination thereof, as desired for other attachments.

When it is desired to mix the components, one component, such as fibrinogen, which, for example is located in the left dispenser is allowed to from one (or first) side of the mixer to another (or second) side of the mixer thereby allowing flow into the other container 908 on the right side of the mixer, where, for example, thrombin is located. It is contemplated that either one or both of the containers may be partially filled prior to mixing to accommodate the additional volume of the other component. The two components are preferably allowed to flow from the container 908 through the mixer to the left side of the mixer. Each time the components pass through the mixing device 900 further mixing between the components is provided.

It is contemplated that the components may pass through the mixing device 900 at least once, but more preferably several times, as desired or necessary to achieve sufficient mixing. For example, where fibrinogen and thrombin are employed, it may be desired to allow the components to pass through the mixing device back and forth between the two containers at least two or three times to achieve sufficient mixing. The mixture may then be stored in one of the containers 906, 908 and detached from the other to permit dispensing at a desired location. For example, the container can be docked on a dispensing system such as the DUPLOJ-ECT applicator from Baxter Healthcare Corporation.

Alternately, a device, as shown and described below at FIGS. 50A-50C, may include a separate nozzle or exit port transfer through which the mixed fluid may be dispensed. It may further be desired to employ the mixing device of FIG. 48 to mix fibrinogen and thrombin and air. For example, one of the containers 910, 912 may contain 1 ml of fibrinogen which may also contain one or more additive agents as described below and having about a 100 mg/ml concentration and the other may contain 1 ml of thrombin, for example, of a 4 IU thrombin concentration, and 2.5 ml of air with the mixing device located between the two containers for transferring the components back and forth between the two containers at least once, and preferably, several times, and, more preferably, at least four times, to create a "fibrin mousse" that is a fibrin mixture having a relatively higher volume of air (such as 125% by air volume in the above example), and a lower density than fibrin mixed without air. The fibrin mousse may, for example, allow application to the underside of a patient's body, such as for treatment of acute or chronic injuries such as a foot ulcer injury. Other volumes of fibrinogen and thrombin, and having different relative amounts, may be combined with different volumes of air to increase or decrease the percentage of air contained in the combined fibrin mixture. The fibrin mousse obtained may also be spray dried to form fully or partially polymerized beads, lyophilized to form a sponge or grinded to obtain a hemaostatic powder (dry fibrin glue), as described in U.S. Pat. No. 7,135,027, as incorporated herein by reference. Other variations are also possible, including mixing of different liquid components for other fields of application, such as egg whites and oil and/or water for the food industry, oil and water or diesel and water for the automotive industry, as well as other applications described further below. Alternatively, it is also possible to mix two or more gases employing the mixing device of FIG. 48.

As previously described devices and systems described herein are not limited to mixing liquid components. One or both of the components may in fact be a gas such as air or other gases. The embodiment shown in FIG. 48 is particularly well suited for mixing a liquid with a gas. In an example involving fibrin formulation, one of the fibrin-forming components may include a selected amount of air and some are discussed further below, although other liquid-gas mixtures are also possible. In this regard, testing utilizing a device such as is shown in FIG. 48 has suggested that the number of transfers between the dispensers or containers does not have a significant impact on the diameter of the bubbles formed when mixing fibrinogen or thrombin with air to produce a foam. On the other hand, it is believed that the type of material utilized for the mixer (relative to its K value) and the air fraction influence the diameter of the bubble formed. That is, once the material has been transferred four times between the containers using a Vyon-F mixing device, a homogenous foam with an average bubble diameter of approximately 50 µm is formed, and additional transfers do not change the diameter or the size dispersion (normalized fluctuation of the average bubble diameter) appreciably. On the other hand, increasing the air fraction from 50% to 70% may increase the average bubble diameter from approximately 50 µm to approximately 65 µm, as may changing the material used as the mixer. It is further believed that the results of testing using fibrinogen are applicable to fibrin as well.

It is also possible for one or more of the components to be a solid that may be passed through a mixer in any one of the devices and systems described herein. The solid is comprised of particles having a size or diameter that is relatively smaller than the minimum pore size of the mixer so that such solid may pass through the mixer. For example, one or more solids may be mixed with another solid, a liquid or a gas as, for example, in methods for making nano or micro sized particles and suspensions thereof.

Figure 49:
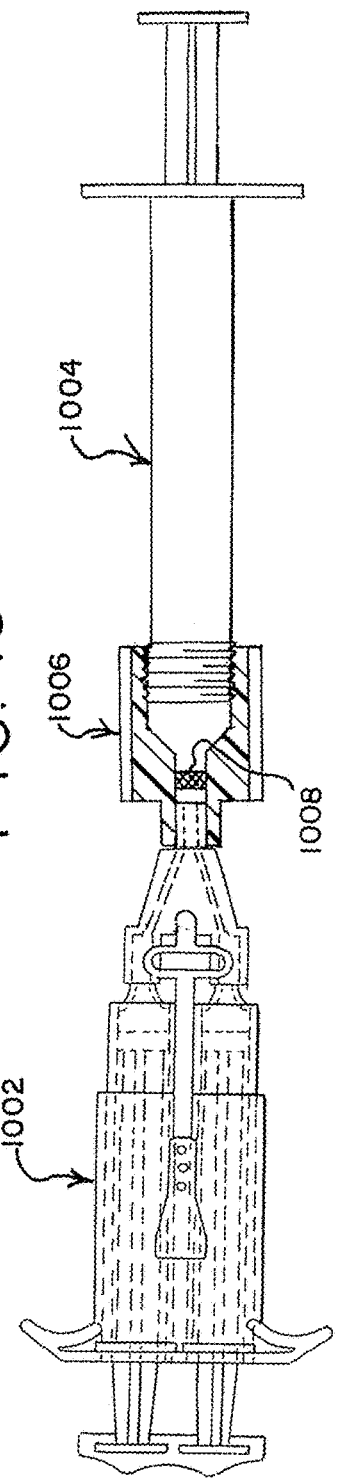
FIG. 49 is a top view of yet another arrangement that includes two dispensing devices connected by a different mixing device.

In accordance with another aspect of the present invention, three or more components may be mixed together using any of the above described embodiments or the like. For example, in FIG. 49 shows first and second devices 1002 and 1004 connected to one another via a mixing device 1006 that employs at least one mixer 1008 located therein. The first device 1002, which may be similar to the dispensers 2, 102, 202, and 302, as described above, may employ at least two containers each separately containing a component, such as one of fibrinogen or thrombin, for mixing. The second device 1004 may contain biphasic calcium phosphate granules. When mixing is desired, the fibrinogen and thrombin may be allowed to flow from the first device 1002 through the mixing device of the mixing device 1006, to provide mixing between the two components into a fibrin mixture, which then is allowed to flow into the second device 1004 to fill the porous spaces around the granules. The second device 1004 may be disconnected for application, for example, to aid bone growth for a patient. Other methods for mixing of the present invention are also possible.

Figure 50A:
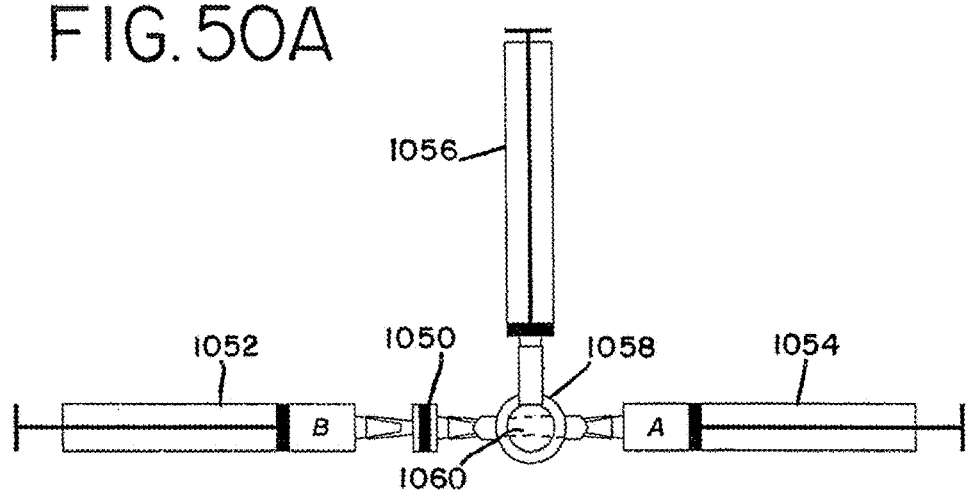
FIGS. 50A-50C depict schematic views of a modified embodiment, similar to FIG. 48, further including a reservoir for receiving or storing the combined fluid stream for various applications.
Figure 50B:
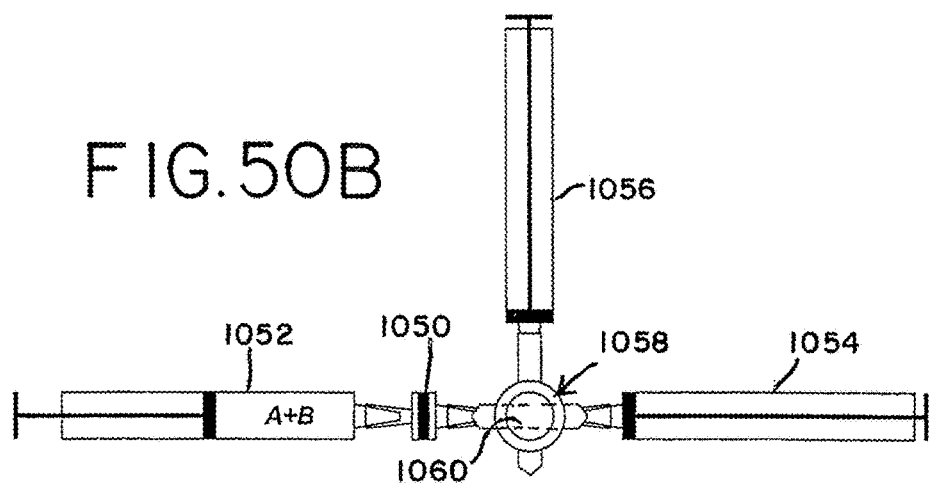
Figure 50C:
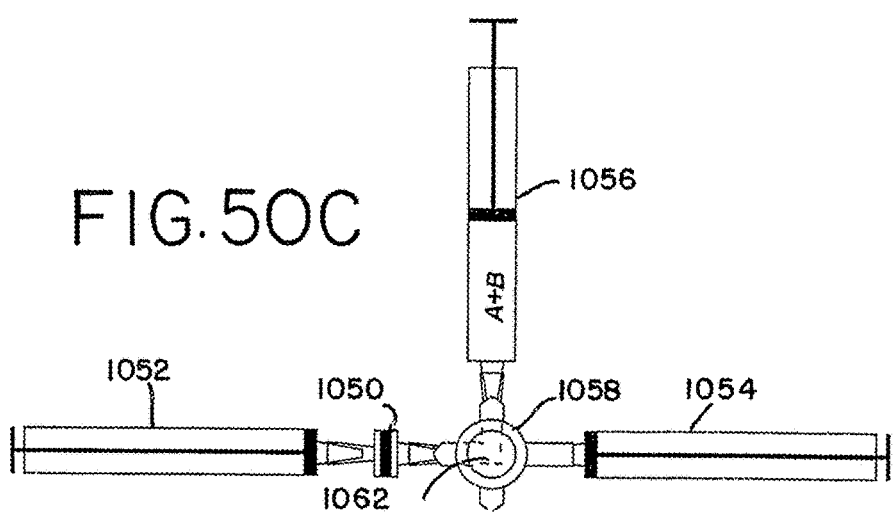

Turning to FIGS. 50A-50C, a modified mixing device 1050 is provided between two containers, 1052 and 1054, and, as such, is similar to the mixing device shown in FIG. 48, and further includes a third container 1056. Each of the containers 1052, 1054 and 1056 are connected by way of a valve 1058 (with the mixing device 1050 being shown at the left side of the valve), such as a three-way value, stop cock or other suitable valve structure which allows selected communication between at least two containers at a selected time. Other variations to the illustrated arrangement are also possible. For example, it is possible to employ one or more mixing devices at either side of the valve and/or to employ two or more mixing devices at any one side of the valve.

By way of example, FIG. 50A shows the first container 1052 and the second container 1054 in fluid communication with each other across the valve 1058 via a fluid passageway 1060. In FIG. 50A, the valve is open to allow for fluid flow between the two containers while fluid flow to the third container 1056 across the valve 1058 is closed. Each container 1052 and 1054 contains at least one component, respectively identified as A and B for mixing into a combined mixture.

As shown in FIGS. 50A and 50B, the component A from container 1054 is allowed to flow across the valve 1058 through the open fluid passageway 1060 and the mixing device 1050 to the container 1052 on the other side of the mixing device 1050 such that both components A+B reside in the same container. In FIGS. 50A-50C, the components A+B may be allowed to flow between the first and second containers 1052 and 1054 at least once (i.e., to container 1054) as a combined mixture and perhaps several times (i.e., back and forth between containers 1052 and 1054) to achieve the desired number of changes in flow direction that provides sufficient mixing of such components using the mixing device. In FIGS. 50A-50C, which employs a single mixing device, it may be desirable to switch the direction of flow several times, although the number of changes in flow direction may be reduced as the number of mixing devices that may be employed is increased. When the desired number of changes in flow direction has occurred, the components A+B preferably reside in one of the containers 1052 and 1054, such as shown in FIG. 50B, which shows components A+B in the same container 1052.

In FIG. 50C, the position of the valve 1058 is rotated to provide a fluid passageway 1062 between one of the containers 1052 and the third container 1056. The flow of the combined mixture A+B is then allowed to flow into the third container 1056, which may be a reservoir or other structure that utilizes the combined mixture. By way of example and not limitation, the third container 1056 may be cylinder of an engine or a reservoir that is in fluid communication with the engine and each component A, B selected from one of a liquid or gas or a mixture of liquid or gas, such as water, air, alcohol (including, for example, ethanol or butanol), oil (including, for example, non-petroleum-based oils), olechemical derivatives, gasoline, diesel, synthetic fuel (such as may be made from carbon monoxide, hydrogen, carbon dioxide and/or some combination thereof) and/or some combination thereof. Such application may be beneficial to provide inline mixing of biodiesel fuel, super oxygenated fuel, fuel/water emulsions, fuel additives or other desired automotive mixtures.

In particular, the alcohol, oil, olechemical derivative, etc. used in such a combination may come from biological sources, rather than being a petroleum product. For example, bioethanol may be produced from feedstocks, such as barley, grapes, maize, wheat, potatoes, sugar beets, and sugar cane. Bioethanol may also be produced from other materials high in starch content, even waste streams from distillation processes used with wine or molasses may be used. Biobutonol may be produced by microbes (which may be genetically-modified for this purpose) as they digest the sugar produced by breaking down cellulosic biomass, such as plant fibers from sources such as grass clippings, tree cuttings, wood chips, and rice straw, or such as may be found in household or animal waste. The non-petroleum oils used in such a combination may include, cotton oil, soy oil, colza oil, palm oil, animal fats, vegetable oil (including hydrogenated vegetable oil), rapeseed oil, sunflower seed oil, jatropha oil, tung oil, coconut oil, tempura oil, and castor oil. The oils may in fact be produced by and harvested from certain forms of oil-producing microalgae, such as is documented in A Look Back at the US Department of Energy's Aquatic Species Program—Biodiesel from Algae, J. Sheehan et al. (July 1998) (cataloging over 3000 strains of oil-producing microalgae). In addition, olechemical derivatives may be used, such as fatty acid methyl esters (FAMES).

An example of forming biodiesel fuel employing the device in FIGS. 50A-50C may include 0.13 ml of water and 0.77 ml gasoline or diesel that is "swooshed" back and forth between containers A and B and then allowed to collect in the third container for immediate use or to be stored for later use. A further example of forming a biofuel mixture employing the device in FIG. 48 may include a 90:10 ratio of ethanol and oil wherein 4 ml of ethanol and 0.4 ml of oil, such as machine oil, is "swooshed" back and forth between the two containers to form a suspension or emulsion. Still another example of forming a biofuel mixture employing a device similar to that in FIG. 48 with a disc of BRM 60 material may include a 8:1 ratio of diesel and oil wherein 8 ml of diesel and 1 ml of oil is "swooshed" back and forth between the two containers to form a solution. An example of super oxygenated fuel employing the device in FIGS. 50A-50C may include 2.0 ml of air and 1.0 ml diesel that is similarly allowed to "swoosh" back and forth between the two containers, in a desired number of times, before passing into the third container for use. Other fields of application are also possible.

It may be preferable to have the above described mixing system available at a service or fuel station where the fuel components are mixed just prior to dispensing by a user into an automobile for use. Alternatively, it may be more preferable to have the mixing system as part of automobile fuel system where the fuel components are mixed just prior to use by the automobile (e.g., just prior to when the fuel mixture is introduced into the cylinder or other combustion device). According to those embodiments utilizing water in the mixture, it is contemplated that the water may be obtained from a water reservoir located in the automobile that may be filled by the driver at home or at a gasoline station and/or may be collected from the air conditioning system, rain and/or other methods.

In addition to the medical and automotive applications already described above, any of the inline mixing devices, as described herein, may be employed in other applications. Examples of such other applications include aerospace (e.g., space propulsion), chemical (e.g., mixtures of cosmetics, paint, detergents and the manufacture of foams, in particular foams utilizing non-petroleum-based polyols), food (e.g., drink mixtures, food additives), PVC or polymer emulsions cosmetics, dental, health or pharmaceutical, adhesives and water treatment (water additives), oil drilling fluids (mixing pressurized water). In addition, such inline mixing devices may be employed in ophthalmologic applications such as to mix and dispense relatively small quantities such as, at about 50 microliters, which may typically require dispensing to a patient at a relatively slow flow rate. As described and shown below, dispensers using one or two mixers, as described herein, achieved relatively good quality of mixing, that is independent of the flow rate employed. In this regard, it is contemplated that the mixers described herein may be employed in other medical and non-medical applications to achieve sufficiently good quality of mixing regardless of the relatively high or low flow rates that may be employed.

In regard to food applications, the mixing devices described above may be used to mix any number of food products. As one example, an egg white may be mixed with air to create an egg white mousse. In such example, one of the containers A and B of the device in FIGS. 50A-50C may contain 2.5 ml of air and the other may contain 0.5 ml of egg white. Alternatively, the mixing device may be used for other food mixtures such as egg yolk with olive oil to create a mayonnaise mixture, vegetable oil and vinegar to create vinaigrette or other food mixtures. Another example, which example may illustrate the use of the mixing devices to combine highly viscous, non-Newtonian fluids, involves the use of a device similar to that in FIGS. 20 and 21 to mix the vanilla and chocolate components of the DANETTE DOUBLE SAVEUR, manufactured and sold by Groupe Danone of Paris, France. The vanilla and chocolate components may have a range of viscosities of between 1660 and 34700 mPa·s (cps) at 4 C and between 890 and 17200 mPa·s (cps) at 20 C, depending on the rate at which the material is agitated. Passage of the material through the mixing device produces a product having a visually uniform color and appearance. As further examples, a whipped cream foam may be formed using the device in FIG. 48 wherein one syringe may contain 3 ml of air and the other may contain 1.5 ml of cream with the air passed into the other syringe first and "swooshed" at least six times (although with a reduction in the amount of air and an increase in the number of transfers, butter may be produced instead), and a gelatin foam may be similarly formed wherein one syringe may contain 2 ml of gelatin solution (5 g of gelatin to 50 ml of water) and the other may contain 3 ml with the materials again "swooshed" at least six times.

It will also be recognized that mixing devices, similar to that in FIGS. 20 and 21, for example, may be used to mix fibrinogen and thrombin to produce a product that may be consumed as food, either by humans or by animals. For example, an extruded food product, similar in shape and appearance to spaghetti, may be formed using 5 ml of beef protein and 5 ml of thrombin. It will be recognized that such an example is not limited to the use of beef protein, but other forms of animal protein may be used as well.

In fact, these mixtures may be produced along lines similar to those described elsewhere herein for the production of tissue sealants, except that additives such as fats, minerals and taste enhancers may be introduced to improve the nutritional quality and/or taste of the product. The fibrinogen and thrombin may also be mixed with liquids, solids, and gases to change the texture of the product. The product may be used alone, or in combination with other proteins, such as meat, fish, shellfish, and game. In regard to the former application, the product may be cast or molded in a particular shape to have the appearance of a particular food item, such as spaghetti, a steak, a nugget, etc. In the latter application of this technology, the product of the mixing devices may be used to bind smaller pieces of meat, fish, shellfish and game together to produce food items having a more consistent or a more desirable shape and/or size. Along similar lines, the product may be used to adhere or secure, for example, dissimilar proteins together, such as a strip of bacon to a shrimp or a steak. The product may thereafter be cooked using normal methods, such as boiled in water, oil, etc., baked, fried, or grilled. Potential uses may also include pharmaceutical products, pet foods, and animal feeds.

In regard to a dental application, a mixing device similar to that in FIG. 48 may be used, for example, to mix alginate and water to form alginate impression material. This example also illustrates the ability of the mixers and mixing methods described herein to mix solid particles and a liquid. The device used in this example included a disc of BRM 60 material. In particular, 1 g of alginate, available as PLAST-ALGIN ORTHO manufactured and sold by Septodont Healthcare of India, and 2.5 ml of water is "swooshed" back and forth between the two containers to form an alginate paste.

In regard to a health or pharmaceutical application, a mixing device similar to that in FIG. 48 may be used, for example, to form an emulsion. According to this example, an oily phase is prepared from 200 ml of soya oil and 12 g of egg phosphatide, while an aqueous phase is prepared from 0.3 g of sodium oleate, 25 g of glycerol and 200 ml of water. In particular, the sodium oleate and glycerol are added to the water after the water has been warmed to 75 C, and mixed using a ULTRA TURRAX T25 mixer (manufactured and sold by IKA-Werke GmbH & Co. KG of Germany) at lowest speed. Similarly, the egg phosphatide is added to the oil after the oil is has been warmed to 65 C, and mixed using an ULTRA TURRAX T25 mixer at 8000-10000 rpm while heating to 75 C. The device used in this example included a disc of Vyon-F material. 2.5 ml of the oily phase and 2.5 ml of the aqueous phase are combined by first pushing the oily phase into the aqueous phase, and the transfer repeated 5-30 times. The results of the testing produced an emulsion that retained its stability for several hours, with an average bubble diameter of between 5-6 μm.

Figure 51:
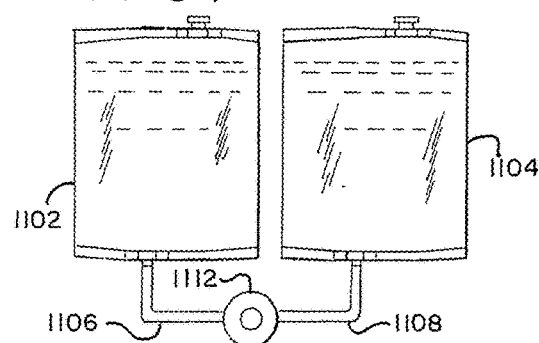
FIG. 51 is a plan view of a further embodiment set forth in the present disclosure showing an infusion system employing a mixing device.
Figure 52:
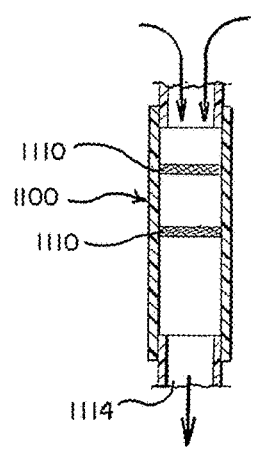
FIG. 52 is an enlarged cross section of a portion of the system of FIG. 50 with other portions shown removed.

FIGS. 51-52 show yet another connector 1100 which, for example, may be employed in an in-line tubing apparatus or method to mix two or more liquids during an infusion delivery to a patient. In FIG. 51, two containers or bags 1102 and 1104 each separately contain a different fluid, for delivery or infusion to a patient. By way of example and not limitation, the fluids may include dextrose and bicarbonate although other fluid is possible. Infusion may be aided by gravity, pump and/or other convention methods. Each container fluidly communicates with a respective passageway 1106 and 1108 which extends downstream to the connector 1100. As previously described with the above embodiments, the connector 1100 may include at least one mixing device or more, with two mixing devices 1110 being shown in FIG. 52 by way of example. The separate passageways 1106 and 1108 are preferably allowed to join together at a selected location 1112 upstream of the connector 1100. The fluid streams pass through the mixing devices 1110 to a passageway 1114 located downstream of the connector 1100 for delivery of the mixture to the patient.

Figure 53:
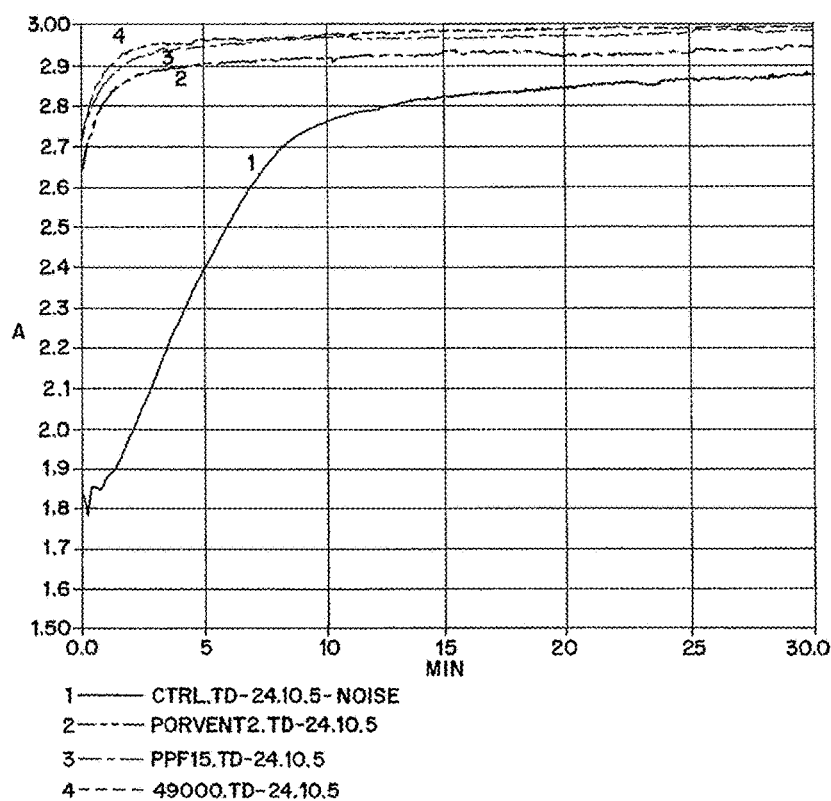
FIGS. 53-54 graphically show the turbidimetry measurements of different fibrin matrices employing different dispensing apparatus.

Any of the devices and systems described herein may be employed as part of a disposable kit, such as a sterile disposable kit for medical applications. The kit may comprise, for example, any one or more of the dispensing/collecting devices or containers shown in FIGS. 1-8 and 18-52, packaged together with a mixer arrangement, as shown in any of FIG. 1-4 or 18-52. The mixer may be already connected together with the dispensing/collecting device or may be a separately packaged or stand alone article that may be assembled to such device.

Where the devices and systems described above are used to prepare a fibrin tissue sealant, a high quality of mixing of a combined fibrin fluid stream, may be characterized by an essentially homogeneous quality (which may be a white color for fibrin obtained with a low thrombin concentration or may be a more transparent appearance for fibrin having a relatively higher thrombin concentration) and a minimum amount of transparent, free liquid, which occurs when the fibrinogen component is essentially homogeneously polymerized with the thrombin component. Accordingly, as shown in FIG. 53, the quality of mixing of fibrin may be estimated by turbidimetry measurements which graphically show the absorbance of light of a fibrin matrix. In FIG. 52 the abscissa represents the change in turbidity based on the optical density (OD) of a dispensed component, such as fibrin, that is monitored at 405 nanometers (nm) with a spectrophotometer, and where the ordinate represents time in minutes. Further explanation of turbidimetry measurements for a fibrin combined fluid stream is provided in "Alteration of Fibrin Network by Activated Protein C", by András Gruber, et al. *Blood*, Vol. 83, No. 9 (May 1, 1994); pp. 2541-2548, which is incorporated herein by reference.

As shown in FIG. 53, such turbidimetry measurements were performed based on a fibrin matrix made of essentially similar concentrations, such as, for example, 4 International Units (IU), of fibrinogen and thrombin, although other concentrations or different combinations of concentrations may be employed for each component. Mixing was performed essentially at room temperature, such as, for example, between about 15 and 25 degrees Celsius. At FIG. 53, curve no. 1 represents a control dispenser which lacks any mixer i.e. or mixing device. Curves nos. 2-4 represent three dispensers which include a mixer 36, such as shown in FIGS. 1-4, where the mixer is comprised of three different materials, respectively, Sample 2, PE, a product sold by Porvair (at curve no. 2); another PP product, as sold by Porvair (at curve no. 3); and Sample 7, a product sold by Porex (at curve no. 4). The graph at FIG. 53, essentially shows a correlation between the use of a mixer (at curves nos. 2-4) and a reduction in the time required for essentially homogeneous mixing. At FIG. 53, curves nos. 2, 3 and 4 show that the time required to reach a plateau representing consistent optical density, and thus, essentially homogeneous mixing is achieved is less time (2-3 minutes) for dispensers having a mixer as compared to the time required (>10 minutes) for a control dispenser which lacks such mixer.

Figure 54:
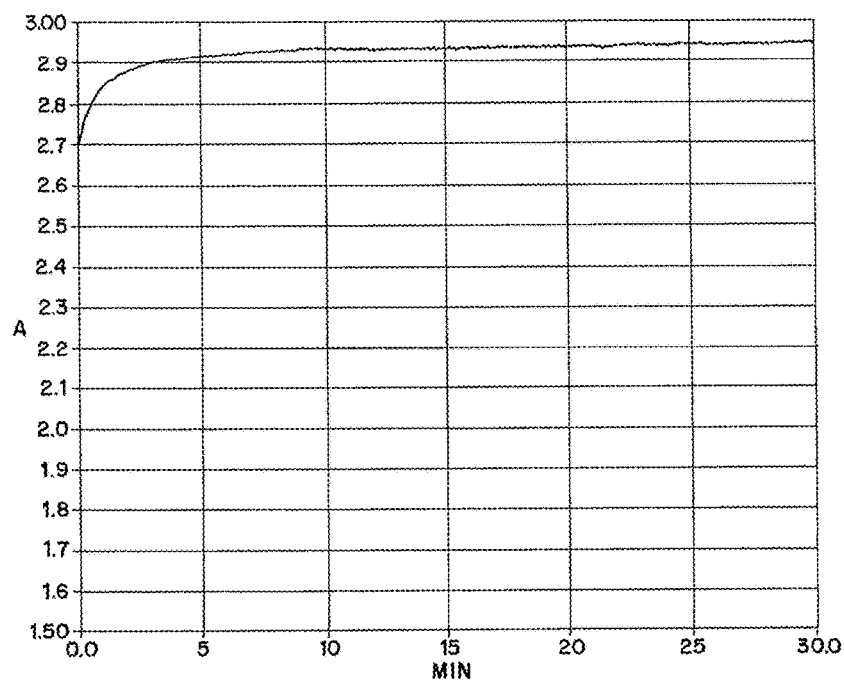

At FIG. 54, the quality of mixing of fibrin is characterized and determined by turbidimetry curve representing two mixers spaced about 4 mm apart and a length L of about 6 mm between the upstream mixer 136A and the distal end 124, such as shown in FIGS. 19-21 and as previously described. The turbidimetry curve of FIG. 53 indicates that the absorbance of light of the combined fibrin fluid stream, reaches a plateau indicative of essentially homogeneous mixing at about 2-3 minutes, similar to above discussed single mixer embodiments The present invention also may provide a combined fluid stream which preferably has a consistent viscosity regardless of temperature. Generally, an increase in temperature improves mixing of components, such as fibrinogen and thrombin. It is noted that the viscosity of fibrinogen varies between about 150 and 250 centipoises (cps) or about 1.5 and 2.5 g/(cm*sec), depending on temperature, which is significantly different, by approximately an order of magnitude, from the viscosity of thrombin, which is between about 10 and 20 centipoises (cps) or about 0.1 and 0.2 g/(cm*sec), also depending on temperature. The present invention may provide for essentially homogeneous mixing at about room temperature without requiring any heating of the components, such as by employing of the above described embodiments.

The quality of mixing of a combined fluid stream, such as fibrin, may also be characterized and determined by adding a contrast or radiopaque agent, such as, for example, Iohexol to the thrombin concentration, prior to mixing of the components. For example, 50, 100, 200, 300, 400, 500 and 600 mg/mL concentrations of Iohexol were separately added to essentially similar thrombin concentrations, such as 75 IU, the concentration of a contrast or radiopaque agent, such as Iohexol, may range between about 50 and 1200 mg/mL, preferably between about 300 and 400 mg/mL. Each thrombin/Iohexol combination may be mixed with a fibrinogen component using a mixer, such as a two-mixer arrangement having a distance V of about 4 mm and a length L of about 6 mm. After passing the components through such mixer, the fibrin samples with Iohexol, as arranged alongside each other, provide more transparent, homogeneously-mixed fibrin streams as compared to a fibrin sample that was obtained without Iohexol using a mixer (indicated at "+" or as arranged alongside the 600 mg/mL sample) which is shown having a white color with greater turbidity. The above described samples were also compared to a "control" fibrin sample without Iohexol and without a mixer. The control sample shown provides a fibrin stream having inconsistent turbidity, viscosity and color which is typical of insufficient mixing. It is possible to use other contrast or radiopaque agents, depending on the desired application and the combined fluid stream to be employed.

It is also possible to add other additive agents, such as antibiotics, drugs or hormones to one or more of the fluid component streams. For example, additives such as Platelet Derived Growth Factor (PDGF) or Parathyroid Hormone (PTH), such as those manufactured for Kuros Biosurgery AG of Zurich, Switzerland, may be added to one of the fibrin-forming components, such as fibrinogen. Bone morphogenic proteins (BMP) may also be employed. By way of example and not limitation, other agents include hydroxypropylmethylcellulose, carboxylmethylcellulose, chitosan, photo-sensitive inhibitors of thrombin and thrombin-like molecules, self assembling amphiphile peptides designed to mimic aggregated collagen fibers (extracellular matrices), catalyst, pro-catalysts, PEG's factor XIII, cross-linking agents, pigments, fibers, polymers, copolymers, antibody, antimicrobial agent, agents for improving the biocompatibility of the structure, proteins, anticoagulants, anti-inflammatory compounds, compounds reducing graft rejection, living cells, cell growth inhibitors, agents stimulating endothelial cells, antibiotics, antiseptics, analgesics, antineoplastics, polypeptides, protease inhibitors, vitamins, cytokine, cytotoxins, minerals, interferons, hormones, polysaccharides, genetic materials, proteins promoting or stimulating the growth and/or attachment of endothelial cells on the cross-linked fibrin, growth factors, growth factors for heparin bond, substances against cholesterol, pain killers, collagen, osteoblasts, drugs, etc. and mixtures thereof. Further examples of such agents also include, but are not limited to, antimicrobial compositions, including antibiotics, such as tetracycline, ciprofloxacin, and the like; antimycogenic compositions; antivirals, such as gangcyclovir, zidovudine, amantidine, vidarabine, ribaravin, trifluridine, acyclovir, dideoxyuridine, and the like, as well as antibodies to viral components or gene products; antifungals, such as diflucan, ketaconizole, nystatin, and the like; and antiparasitic agents, such as pentamidine, and the like. Other agents may further include anti-inflammatory agents, such as alpha- or beta- or .gamma-interferon, alpha- or beta-tumor necrosis factor, and the like, and interleukins.

Other additives may be introduced into one or more of the fluid component streams as well. For example, catalysts, co-catalysts, visualization agents, dyes, markers, tracers, and disinfectants may be included. Particular examples of suitable visualization agents are described in U.S. Pat. Nos. 6,887,974 and 7,211,651, while examples of dyes (e.g., squaraine dyes), markers and tracers are described in U.S. Pat. No. 6,054,122 and PCT Publication No. WO 2008/027821, and disinfectants (e.g., methylene blue) in U.S. Pat.

Nos. 5,989,215, 6,074,663, and 6,461,325, all of which patents and publications are incorporated by reference herein in their entirety.

It is possible that such agents or additives may be pre-mixed with one or more of the fluid components, such as fibrinogen and/or thrombin in the respective component container. Alternatively, it may be possible for such agents or additives to be stored in a separate container as a liquid or lyophilized for mixing with one or more components during use of the dispenser and/or mixer. As a further alternative, the agents or additives could be disposed in the mixing device. As a still further alternative, the agents or additives may be contained in a cartridge that is disposed in the flow line upstream of the mixer.

For a dispenser or mixer, such as in any of the above described embodiments, in which one or more of agents are employed, the combined fluid stream preferably provides a sufficiently thoroughly mixed sealant, such as fibrin sealant, in which the antibiotic, drug, hormone, or other agents may be essentially well dispersed throughout the sealant. Such antibiotic, drug, hormone, or other agent may allow controlled release over time to the applied working surface, for example, to aid in post-operative or surgical treatment. It is contemplated that various agents may be employed depending on the desired application and the combined fluid stream.

Although the present invention has been described as employing at least two separate sources of fluid upstream of the mixer, it is also possible to eliminate one of such sources and provide such source within the formation of one or more mixing devices. For example, for forming a tissue sealant, such as fibrin, thrombin may be adsorbed, either soaked as a liquid or incorporated as a solid, into one or more of the mixers and freeze-dried to provide a source of thrombin. Such a mixing device could be connected or otherwise placed in flow communication with a single source of fibrinogen, such as a single syringe containing fibrinogen at 45 mg/mL, for generating a tissue sealant via the mixing that would occur when the fibrinogen is forced through the mixer. Other wet or dry components may be employed with one or more mixers or different components may be employed on different mixers, where one than one mixer is employed.

Another way to determine and characterize the quality of mixing may include mechanical testing of the combined fluid stream. Such testing may include testing the reactivity of the combined fluid stream to forces such as tension or compression forces. Generally speaking, a sufficiently thoroughly mixed, polymerized and homogeneous fibrin stream may withstand tensioning and compression forces to a greater extent than a fibrin stream which is insufficiently mixed, polymerized and homogeneous. For example, for a fibrin stream, tension may be applied to the fibrin stream along its length to determine the extent of fibrin elongation without separation of the stream. In one example, for two mixers having a distance V of between about 0 and 5 mm, preferably between about 3 and 4 mm, and a length L between about 2 and 6 mm, preferably between about 5 and 6 mm, a resulting fibrin stream may provide a fibrin elongation of about 100% to 300%, although other elongations are also possible. Other types of tests may also be employed for determining the quality of mixing.

FIGS. 55-60 show another way and perhaps preferred way of characterizing and determining the quality of mixing from the mixing device of the present invention, such as for a fibrin mixture. The degree of crosslinking may for example, measure a selected amount of a constituent component chain that is contained in the fibrin mixture to a selected amount of the same constituent component in fibrinogen, prior to mixing. Fibrinogen contains selected amounts of alpha ($\alpha$) monomer chain, albumin, beta ($\beta$) chain and gamma ($\gamma$) chain. After mixing with thrombin to form fibrin, the fibrin contains different amounts of such component chains due to the crosslinking that has occurred. Typically, fibrin contains a reduced amount of alpha monomer and gamma monomer chains, which have polymerized into alpha-alpha pairs or polymers and gamma-gamma pairs or polymers (or gamma dimer) chains. By way of example and not limitation, the degree or rate of crosslinking may measure that amount of reduction in the alpha monomer chain that is present in the fibrin mixture as compared to the amount of such alpha monomer that is present in the fibrinogen prior to mixing.

Figure 55:
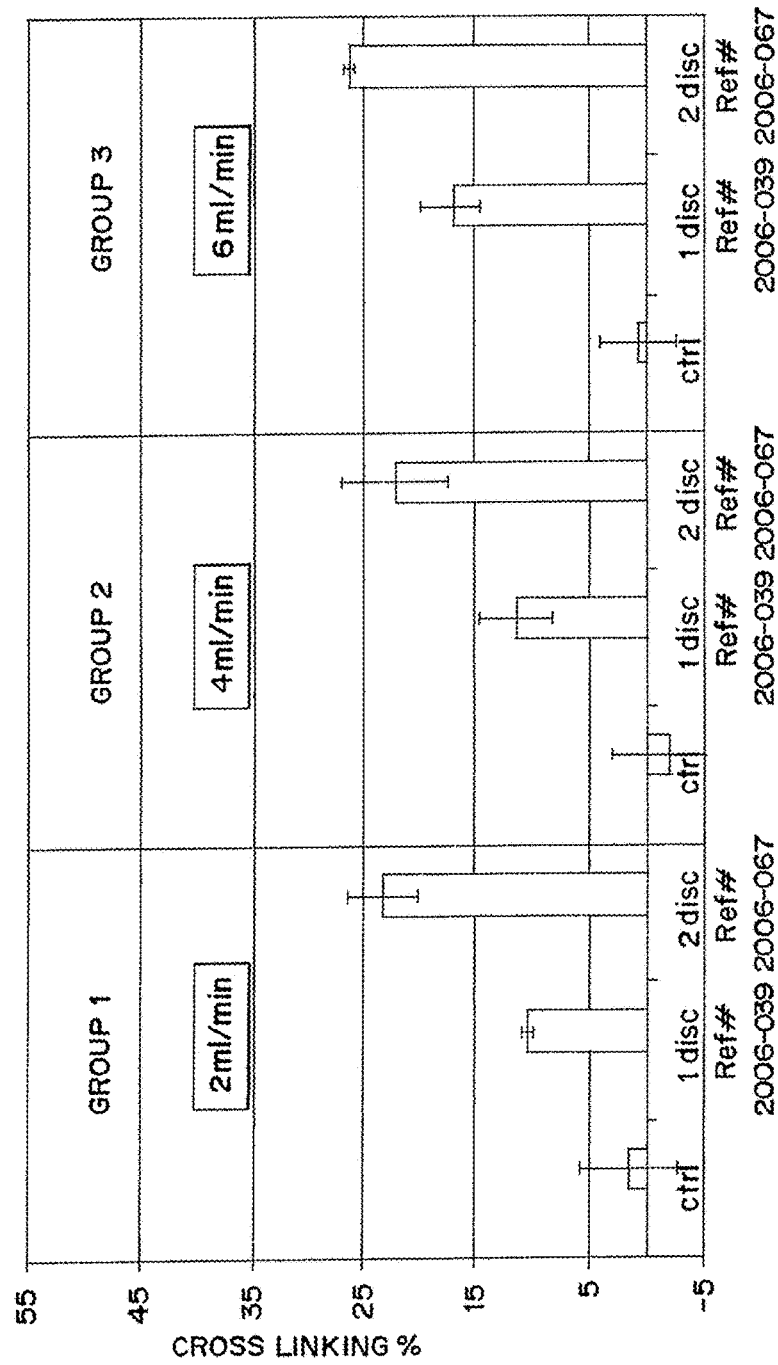
FIG. 55 shows the % crosslinking of alpha (α) monomer chains in different fibrin mixtures for three different groups, each group employing a different flow rate, 2 ml/min, 4 ml/min and 6 ml/min, and each group consisting of results based on three different dispensing devices.

At FIG. 55, the rate of crosslinking is shown for three flow rates of fibrin, at 2 ml/min for Group 1, at 4 ml/min for Group 2, and at 6 ml/min for Group 3. At each flow rate, at least one fibrin sample was separately analyzed for each of the following devices: a control device, which lacked a mixing device; a single mixing device made of polyethylene (PE), having a thickness of 1.5 mm and placed 2 mm from the distal end (such as a dispensing housing having a distal end overmolded on a needle or cannula having a single mixer); and a double mixing device made of polyethylene (PE), having thickness of 1.5 mm, and having a distance between the mixing devices of about 4 mm and a distance between the end of the dispensing distal end and the first mixing device of about 4 mm. As shown in FIG. 55, the rate of crosslinking of the non-mixing device ranges between about 0-2%. The rate of crosslinking for the single mixing device ranges between about 10-20%, preferably 10-16%. The rate of crosslinking for the double mixing device ranges between about 20-30%, preferably 23-36%. As shown in FIG. 55, the rate of crosslinking of fibrin obtained using one or two mixing devices at each flow rate is generally consistent regardless of the flow rate employed.

The degree of alpha-$\alpha$-chain cross-linking is determined by measuring the reduction overtime of the alpha-$\alpha$-chain-band in comparison to the band containing the fibrin-$\beta$-chain and albumin. An electrophoresis method was performed based on an UREA/SDS electrophoresis technique on a DESAGA electrophoresis system (Sarstedt-Gruppe) loaded with a 5% acryl amid separation gel to identify the different chains of fibrinogen. After mixing fibrinogen and thrombin components at a ratio 1:1, the mixture was incubated at 37 C. The fibrinogen component employed for each of the samples described contained about 3 IU of Factor X III (FXIII) although it is realized that other concentrations of FXIII may be employed, which will achieve difference rates of crosslinking. Generally, crosslinking increases as the amount of FXIII is increased. After an incubation time of 0 and 120 min, the reaction was stopped by addition of a denaturant sample buffer and heated at 70 C for 5 min. The clots were left overnight for dissolution in the sample buffer at room temperature. The samples were loaded on a 5% polyacrylamide/urea gel. The gel was stained with Coomassie Brilliant Blue R250 and destained according to the method of Furlan, as shown on FIG. 56. The amounts of alpha-$\alpha$-chain, beta-$\beta$-chain, gamma-$\gamma$-chain, fibronectin and albumin of samples in FIGS. 55-60 were then determined by densitometry and plotted on drawings represented by FIGS. 57, 58, 59 and 60.

Figure 56:
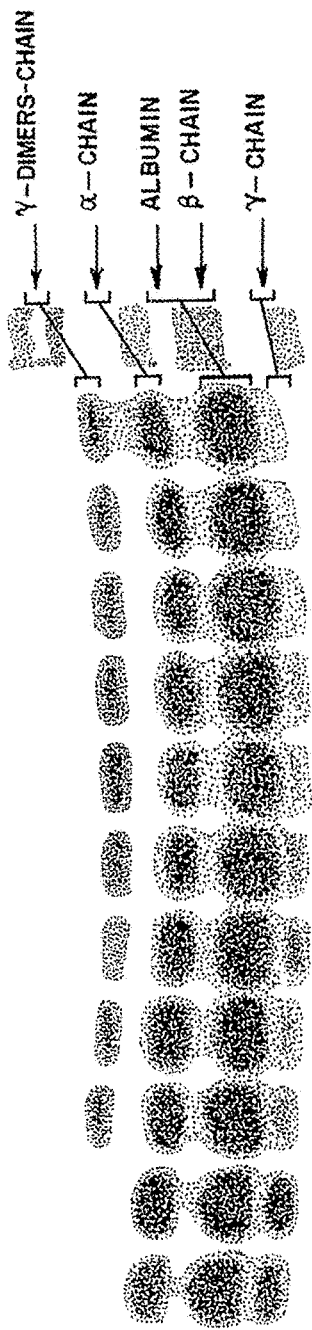
FIG. 56 shows electrophoretic patterns for ten different samples of fibrinogen or fibrin mixtures, which identifies the presence or absence of different constituent components according to the molecular weight of such components.

In FIG. 56, 12 lanes of horizontal bands are shown that were prepared according to the electrophoresis procedure described above including a marker or baseline at lane 12 for purposes of quality control for such procedure. In FIG. 56, the "zero sample 1" and "zero sample 2" indicate the presence of constituent components, according to molecular weight, in fibrinogen at an incubation time zero, and thus before any crosslinking with thrombin has occurred. Samples 10-18 show the presence of the constituent components in a fibrin mixture after an incubation time of 120 minutes, according to the different devices represented in Group 2 of FIG. 55. More particularly, samples 10-12 correspond to the results obtained without employing a mixing device (corresponding to "ctrl" at 4 ml/min in FIG. 55), samples 13-15 show the results obtained by employing one mixing device (corresponding to "1 disc" at 4 ml/min in FIG. 55), and samples 16-18 show the results obtained by employing two mixing devices (corresponding "2 disc" at 4 ml/min in FIG. 55). At shown in FIG. 56, each of the "zero samples" and samples 10-18 contains selected amounts of alpha (α) monomer chain, a combined albumin+beta (β) chain and gamma (γ) chain, as indicated by the respective bands illustrated for each sample. Also in FIG. 56, each of samples 10-18 alpha (α) polymer chain, as indicated at the top of samples 10-18, and gamma (γ) polymer (or gamma dimer) chain, located above the alpha monomer chain are present. Such chains are typically present after crosslinking has occurred due to mixing of the fibrinogen and thrombin components, and thus are generally absent or negligible in the "zero samples" shown in FIG. 56. Typically, a darker band indicates a greater amount of a constituent chain. In FIG. 56, samples 13-18, which employ at least one more mixing devices, have darker alpha (α) polymer and gamma (γ) polymer (or gamma dimer) chains, which correspond to the greater crosslinking values shown in FIG. 55.

Figure 57:
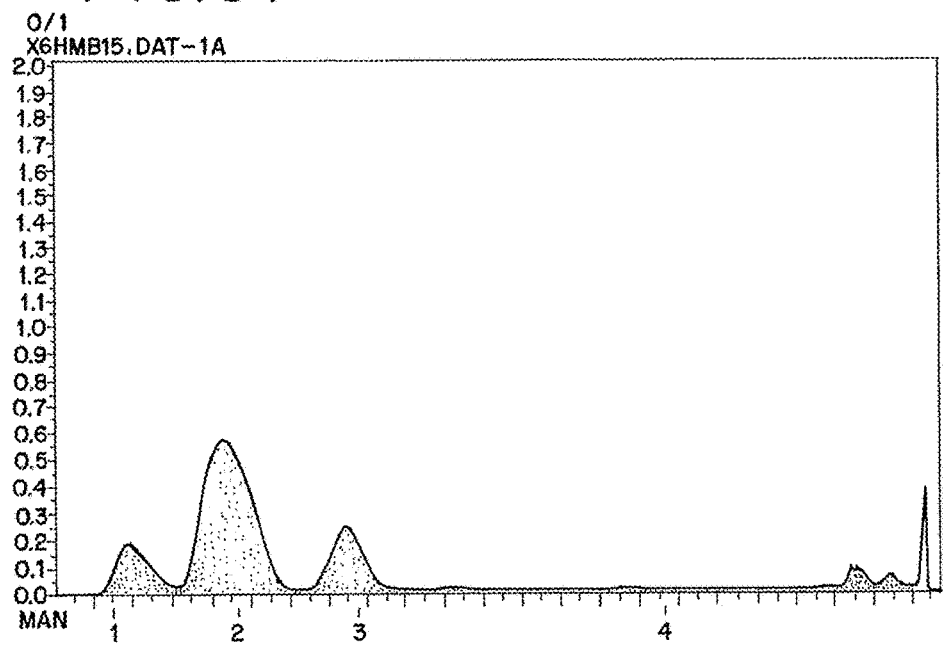

Turning to FIG. 57, the relative amounts of the constituent chains contained in the "zero samples" are shown which include 3 peaks along the graph, labeled at 1, 2 and 3. Respectively, such peaks correspond to the amount of the gamma (γ) monomer chain at peak 1, the amount of the albumin+beta (β)-chain at peak 2, and the amount of the alpha-(α)-chain at peak 3. If present, the amount of the gamma polymer or gamma dimer chain would be represented above the label at peak 4 and the amount of alpha polymer chain would be represented above the label at peak 5, (although little if any measurable peak can be seen due to mixing with thrombin not yet occurring. Based on the data represented in FIG. 57, the relative amounts of alpha-(α)-Monomer chain to beta-(β)-Monomer chain plus albumin can be calculated by integration of the area under each respective peak as follows:

TABLE 4

| Number | Total |
|---|---|
| 1 | 19.712 |
| 2 | 84.771 |
| 3 | 26.619 |
| 4 | 24.411 |

Figure 58:
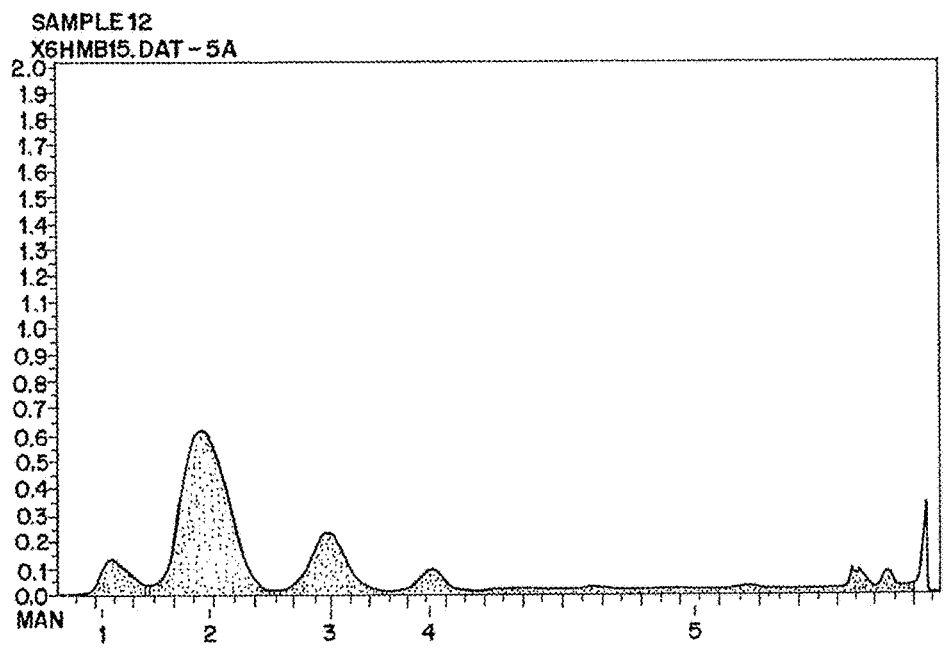

FIGS. 58-60 show the relative amounts of selected constituent components contained in sample 12—one of the control samples from FIG. 56, sample 13—one of the single mixing device samples—and sample 17—one of the two mixing device samples—and their respective peaks at 1, 2, 3 and 4 corresponding to the amount of the gamma monomer chain at peak 1, the amount of the albumin+beta-(β)-chain at peak 2, and the amount of the alpha-(α)-monomer chain at peak 3, and the amount of the gamma polymer or gamma dimer chain at peak 4, representing some crosslinking reaction due to the mixing of fibrinogen and thrombin. Based on integrating the area under the respective peaks in FIGS. 58-60, the relative amounts of such chains are calculated as follows:

TABLE 5

| Number - chain | Totals from Sample 12 | Totals from Sample 13 | Totals from Sample 17 |
|---|---|---|---|
| 1 - γ monomer | 12.932 | 5.486 | 4.077 |
| 2 - albumin + β | 82.833 | 87.718 | 77.378 |
| 3 - α monomer | 26.714 | 24.821 | 19.444 |
| 4 - γ dimer | 8.390 | 14.825 | 13.044 |

The degree of crosslinking may be represented as a Q value:

$$Q = X_n/X_1,$$

where $X_1$ represents the ratio or quotient of the total alpha α chain (total at peak 3) to the total albumin+β chain (total at peak 2) from Table 4 for an incubation time zero (0) (time) or for fibrinogen prior to mixing with thrombin; and $X_n$ represents the ratio or quotient of the total alpha α chain (total at peak 3) to the total albumin+β chain (total at peak 2) for any one of the samples indicated in Table 5 for an incubation time n or for a fibrin mixture after mixing with thrombin.

Based on the above samples, the estimated crosslinking or Q values may be represented as follows:

TABLE 6

| Value | Sample 0/1 - Fibrinogen | Sample 12 | Sample 13 | Sample 17 |
|---|---|---|---|---|
| α monomer/ (albumin + β) | 26.619/ 84.771 | 26.714/ 82.833 | 24.821/ 87.718 | 19.444/ 77.378 |
| X1 = α monomer/ (albumin + β) | 0.314 | 0.314 | 0.314 | 0.314 |
| $X_n$ = α monomer/ (albumin + β) | — | 0.322 | 0.282 | 0.251 |
| $X_n/X_1$ | 0.314 | 0.322/ 0.314 | 0.282/ 0.314 | 0.251/ 0.314 |
| Q | — | 1.0 | 0.89 | 0.79 |
| % crosslinking | | 0 | 11 | 21 |

Based on the above examples, $X_1$ may be represented as $X_1$=alpha α chain/albumin+β chain from "Zero Sample" or fibrinogen prior to mixing. For example, $X_1$ may have a value of about 26.619/84.771 or about 0.314, as indicated above. $X_n$ may be represented as $X_n$=alpha α chain/albumin+β chain for any one of the fibrin mixtures of Samples 12, 13 or 17, as indicated above, for example, in sample 17, $X_n$ may have a value of about 19.444/77.378 or about 0.251. The incubation time employed in the above examples is about 120 minutes and were observed at a temperature of 37 degrees Celsius, although other incubation times and temperatures may be employed. The rate of crosslinking further may be represented as a percentage, which is also indicated in the above table and may be calculated as follows:

Rate of crosslinking [%]: $100 \times (1-Q)$

As shown in Table 6 above the quality of mixing as determined by the rate of alpha chain crosslinking was improved in devices using at least one mixer and further improved when two mixers are used. As shown in Table 6 the % crosslinking reported was approximately 11% and within a typical range of approximately 10-16%. The % crosslinking in devices using two mixers was approximately 21% and within a range of about 20%-30%.

Figure 61:
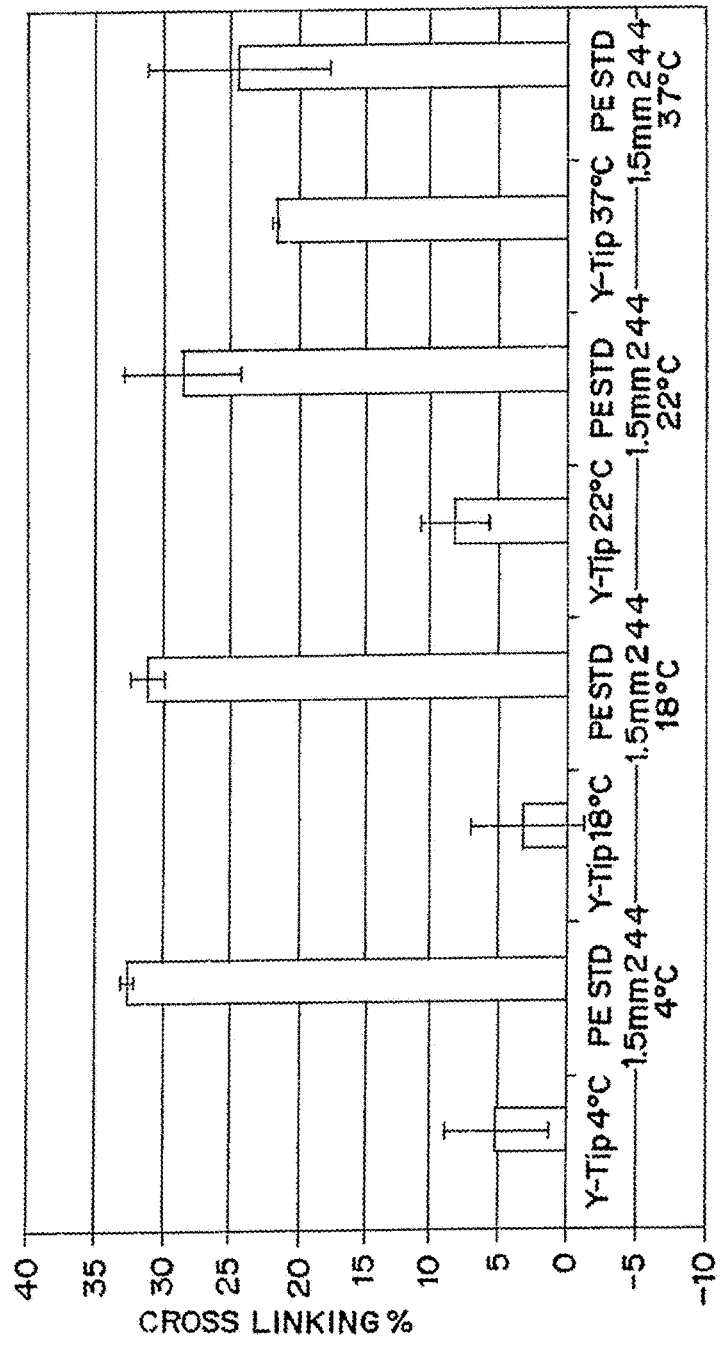
FIG. 61 shows the % crosslinking of alpha (α) monomer chains in different fibrin mixtures at different temperatures—4° C., 18° C., 22° C., 37° C.

In FIG. 61, the data shown indicates the effect of temperature on the quality of fibrin mixing formed with a two mixer device, such as shown in FIGS. 19-21. For example, the distance between the mixers may be 4 mm and the distance from the y piece to the first mixer may be 4 mm, with a thickness of 1.5 mm. The data represents the rate of crosslinking of a fibrin mixture at each of temperatures 4° C., 18° C., 22° C. and 37° C. for each of a control device without a mixer as compared to using a mixing device, as described above.

As represented in FIG. 61, the % crosslinking for fibrin obtained by using the mixing device ranged between about 24-33% with the highest valve obtained at 4° C., a temperature at which fibrinogen has an estimated viscosity of between about 500-600 cps. At 18° C. and 22° C. the viscosity of fibrinogen ranges between about 160 cps to 120 cps and at 37° C., the viscosity of fibrinogen is between about 70-80 cps and thrombin is about 5 cps. Other lots may show different viscosity. As shown, the % crosslinking using the described mixing device is relatively consistent at each represented temperature, as compared to the control device which achieves poor crosslinking at the lower temperatures 4-22° C.

As represented in Table 6, the quality of mixing is not dependent on the temperature when using a mixing device in contrast to the control device which requires an increase to 37° C. to such a value of 21% crosslinking. By way of example, a fibrin mixture using a mixing device in Table 6 would not require heating or warming above typical operating room temperatures of about 18° C. to 22° C., as 27%-33% crosslinking is achieved as such temperature ranges. In addition, the above described % crosslinking is generally not affected by gamma irradiation, or sterilization as applied with the medical field.

Other ways may also be employed to measure the degree of crosslinking, such as for example, measuring the increase or decrease in other constituent chains. By way of example and not limitation, in addition or as an alternative to the above, it is also possible to measure the degree of crosslinking by measuring the increase in one or both of the gamma ($\gamma$) polymer (or gamma ($\gamma$) dimer) chain and the alpha ($\alpha$) polymer chain, as either component generally increases as the degree of crosslinking increases to indicate mixing of the fibrinogen and thrombin. Another way to measure the degree of crosslinking may be measure the decrease in the gamma ($\gamma$) monomer chain, which decreases as the degree of crosslinking increases.

Figure 62:
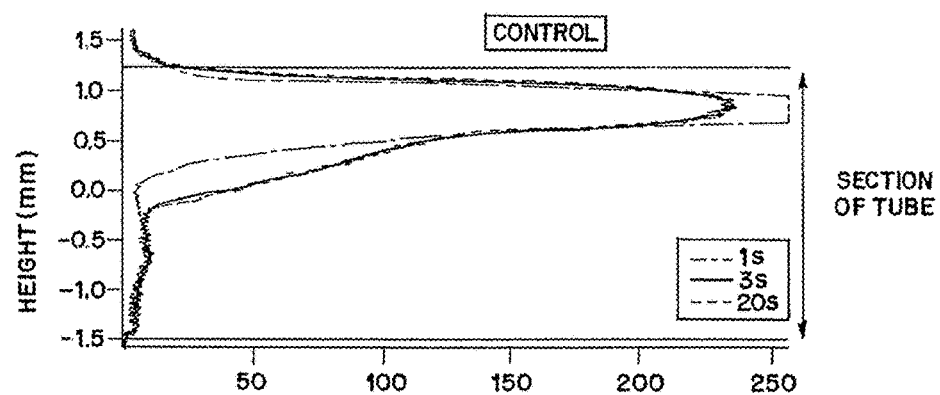
FIGS. 62-63 are graphs showing the degree of fluorescence along a cross-section of tubing for a fibrin mixture, respectively, of an apparatus without a mixer (in FIG. 62) and an apparatus with at least one mixer (in FIG. 63).
Figure 63:
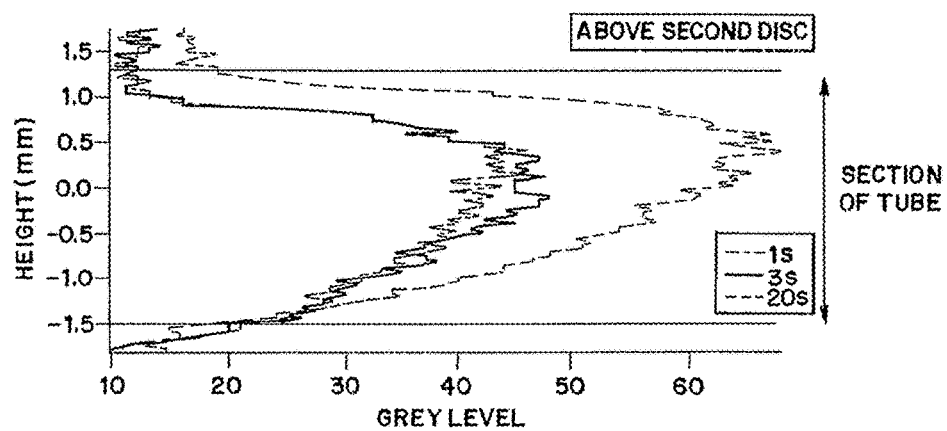

FIGS. 62-63 show yet another way to estimate the quality of mixing from the mixing device of the present invention, such as for a fibrin mixture. For example, the degree of mixing may be determined by monitoring an optical characteristic of the fibrinogen and an optical characteristic of thrombin as compared to the presence of such optical characteristics in the fibrin mixture. As shown in FIGS. 62-63, one such optical characteristic may include the degree of fluorescence emitted from a combined fibrinogen and thrombin fluid stream in the fluid passageway after joining the separated streams of such components.

FIG. 62 shows the distribution of fluorescence in a cross-section of tubing (represented between the two black lines, between 1.2 and −1.5 mm of the tubing section height) for a combined fluid stream of thrombin and fibrinogen and the relative grey level, which ranges between about 0-250, for an apparatus without a mixing device. In contrast, FIG. 63 shows the distribution of fluorescence in a similar section of tubing that is observed downstream a mixing device, such as employing any of the previously described mixing devices. In FIG. 62, the distribution of fluorescence is evaluated after 1, 3 and 20 seconds of flow rate. A relatively high distribution of fluorescence of about 220 to 250 is generally concentrated on one side of the section of tubing between about 0 and 1.2, along the Y-axis, which corresponds to the presence of thrombin that generally has a high degree of fluorescence. A relatively low distribution of fluorescence is indicated on the other side of the section of tubing between about 0 and −1.5, which generally corresponds to the presence of fibrinogen that generally has a low distribution of fluorescence. As represented in FIG. 62, the high distribution of fluorescence along one side of the tubing section and the low distribution of fluorescence on the other side of such tubing section generally indicates that relatively little mixing is achieve between the thrombin and fibrinogen fluid streams.

In contrast, FIG. 63 shows the distribution of fluorescence of a combined fibrinogen and thrombin stream downstream of a mixing device, with respective distribution curves shown for 1, 3 and 20 seconds. As can be seen in FIG. 63, each curve is generally well distributed over the entire tubing section between the range of about 1.2 and −1.5 mm of the tubing section height. It is also possible that other ways may be employed to measure the quality of mixing, such as for example, other optical or physical characteristics of the components.

As can be seen from the above description, the present invention has several different aspects, which are not limited to the specific structures shown in the attached drawings. Variations of these concepts or structures may be embodied in other structures for carrying out application of tissue sealant or other applications in the medical or other fields without departing from the present invention as set forth in the appended claims.

The invention claimed is:

1. A mixing and dispensing assembly for receiving first and second substances and causing the first and second substances to be mixed and then dispensed, the mixing and dispensing assembly comprising:
   a first input port;
   a second input port;
   an output passageway having a receiving end and a dispensing end;
   a first passageway in fluid communication with the first input port and the receiving end of the output passageway and configured to receive the first substance and communicate the first substance from the first input port to the receiving end of the output passageway;
   a second passageway in fluid communication with the second input port and the receiving end of the output passageway and configured to receive the second substance and communicate the second substance from the second input port to the receiving end of the output passageway, wherein the first and second passageways are positioned oblique to one another along their respective lengths and with respect to the output passageway to enable combination of the first and second substances; and
   a first mixing element disposed in the output passageway downstream of the first and second passageways and upstream of the dispensing end, the first mixing element comprising a three-dimensional matrix or lattice that defines a plurality of tortuous, interconnected passageways,
   wherein the first substance and the second substance enter the output passageway from the respective first and second oblique passageways, combining to become partially mixed between the first and second passageways and the first mixing element, and wherein the partially mixed combination of the first and second substances, upon passing through the first mixing element, is further mixed by passing through the tortuous, interconnected passageways in the first mixing element.

2. The mixing and dispensing assembly according to claim 1, wherein the first and second input ports, and the first and second passageways, form a flow director, and wherein the first and second input ports are disposed at a proximal end of the flow director and enter the receiving end of the output passageway at a distal end of the flow director.

3. The mixing and dispensing assembly according to claim 1, wherein the first and second oblique passageways are positioned at respective first and second non-perpendicular angles with respect to the receiving end of the output passageway, wherein the first and second angles are selected to assist in combination of the first and second substances.

4. The mixing and dispensing assembly according to claim 3, wherein the respective first and second angles are selected such that interactions between the first and second substances and a wall of the output passageway facilitate mixing of the first and second substances.

5. The mixing and dispensing assembly according to claim 1, wherein the first mixing element comprises a polymeric material formed by sintering.

6. The mixing and dispensing assembly according to claim 1, wherein the mixing element is disposed downstream of the first and second passageways by a distance, L, between 0 and 6 mm, inclusive.

7. The mixing and dispensing assembly according to claim 6, wherein L is between 1 and 6 mm, inclusive.

8. The mixing and dispensing assembly according to claim 6, wherein L is between 4 and 6 mm, inclusive.

9. The mixing and dispensing assembly according to claim 1, further comprising a second mixing element downstream of the first mixing element and upstream of the dispensing end, the second mixing element comprising a three dimensional matrix or lattice that defines a plurality of tortuous, interconnected passageways.

10. The mixing and dispensing assembly according to claim 9, wherein the first and second mixing elements are separated from one another by a distance, V, between 0 and 6 mm, inclusive.

11. The mixing and dispensing assembly according to claim 10, wherein V is between 3 and 6 mm, inclusive.

12. The mixing and dispensing assembly according to claim 9, wherein the first and second mixing elements differ in one or more of porosity, mean pore size, and length.

13. The mixing and dispensing assembly according to claim 9, wherein each of the first and second mixing elements has a porosity between 20 and 60 percent, inclusive.

14. The mixing and dispensing assembly according to claim 1, wherein the first mixing element has a porosity between 20 and 60 percent, inclusive.

15. The mixing and dispensing assembly according to claim 14, wherein the first mixing element has a porosity between 20 and 50 percent, inclusive.

16. The mixing and dispensing assembly according to claim 14, wherein the first mixing element has a porosity between 20 and 40 percent, inclusive.

17. The mixing and dispensing assembly according to claim 1, wherein the first mixing element is characterized by a mean flow pore size in millimeters, a thickness in millimeters, and a porosity volume as a percent, and wherein the product of mean flow pore size, the thickness, and the porosity volume, multiplied by 1000, is between 16 and 55, inclusive.

18. The mixing and dispensing assembly according to claim 1, further comprising a third passageway for injecting a liquid or gas for the purpose of ejecting, flushing, and/or cleaning the output passageway and/or the first mixing element.

19. A mixing and dispensing assembly for receiving first and second substances and causing the first and second substances to be mixed and then dispensed, the mixing and dispensing assembly comprising:
a first input port;
a second input port, wherein at least one of the first and second input ports is configured to matingly receive a syringe;
an output passageway having a receiving end and a dispensing end;
a first passageway in fluid communication with the first input port and the receiving end of the output passageway and configured to receive the first substance and communicate the first substance from the first input port to the receiving end of the output passageway;
a second passageway in fluid communication with the second input port and the receiving end of the output passageway and configured to receive the second substance and communicate the second substance from the second input port to the receiving end of the output passageway, wherein the first and second passageways are positioned oblique to one another along their respective lengths and with respect to the output passageway to enable combination of the first and second substances; and
a first mixing element disposed in the output passageway downstream of the first and second passageways and upstream of the dispensing end, the first mixing element comprising a three-dimensional matrix or lattice that defines a plurality of tortuous, interconnected passageways,
wherein the first substance and the second substance enter the output passageway from the respective first and second passageways, combining to become partially mixed between the first and second passageways and the first mixing element, and
wherein the partially mixed combination of the first and second substances, upon passing through the first mixing element, is further mixed by passing through the tortuous, interconnected passageways in the first mixing element.

20. The mixing and dispensing assembly according to claim 19, wherein the at least one of first and second input ports includes a luer fitting to matingly receive the syringe.

* * * * *